(12) United States Patent
Kalfas et al.

(10) Patent No.: US 7,645,294 B2
(45) Date of Patent: Jan. 12, 2010

(54) HEAD-TO-HEAD CONNECTOR SPINAL FIXATION SYSTEM

(75) Inventors: Iain H. Kalfas, Beachwood, OH (US);
Carl Lauryssen, Malibu, CA (US);
Steven Ludwig, Severna Park, MD (US);
Michael O'Brien, Pinecrest, FL (US);
Thomas Doherty, Bellingham, MA (US); Mark T. Hall, Bridgewater, MA (US); Bryan S. Jones, Norwood, MA (US); David Konieczynski, Needham, MA (US); Raymond F. Murphy, Attleboro, MA (US)

(73) Assignee: Depuy Spine, Inc., Raynham, MA (US)

( * ) Notice: Subject to any disclaimer, the term of this patent is extended or adjusted under 35 U.S.C. 154(b) by 486 days.

(21) Appl. No.: 10/813,904

(22) Filed: Mar. 31, 2004

(65) Prior Publication Data

US 2005/0228326 A1  Oct. 13, 2005

(51) Int. Cl.
*A61B 17/70* (2006.01)
(52) U.S. Cl. .............. 606/250; 606/246; 606/264; 606/265; 606/266; 606/267
(58) Field of Classification Search .......... 606/61, 606/69–71, 246–321
See application file for complete search history.

(56) References Cited

U.S. PATENT DOCUMENTS

| | | |
|---|---|---|
| 180,881 A | 8/1876 | Howson |
| 457,964 A | 8/1891 | Bolte |
| 483,342 A | 9/1892 | Bolte |
| 596,729 A | 1/1898 | White |
| 900,717 A | 10/1908 | Feaster |
| 1,455,441 A | 5/1923 | La Hodny |
| 2,638,301 A | 5/1953 | Smith |
| 3,019,504 A | 2/1962 | Castagliuolo |

(Continued)

FOREIGN PATENT DOCUMENTS

DE  867422  2/1953

(Continued)

OTHER PUBLICATIONS

Asher, et al., "A Modular Spinal Rod Linkage System to Provide Rotational Stability", SPINE, vol. 13, No. 3, pp. 272-277, 1998.

(Continued)

*Primary Examiner*—Thomas C Barrett
*Assistant Examiner*—Andrew Yang

(57) ABSTRACT

A spinal fixation system comprising at least two bone anchors, a rod connecting the bone anchors and a connecting plate extending from a proximal surface of at least one of the bone anchors. A method of fixing vertebrae relative to each other comprising the steps of: implanting bone anchors in two adjacent vertebrae, each bone anchor having a rod receiving portion; placing a rod in the rod receiving portions, thereby connecting the bone anchors; threadably engaging set screws in the rod receiving portions of at least a portion of the bone anchors, thereby fixing the rod to the bone anchors; mating one end of a connecting plate to a proximal bearing surface of at least a portion of the bone anchors; and engaging a cap with at least a portion of the set screws, thereby fixing the connecting plate to the bone anchors.

40 Claims, 19 Drawing Sheets

U.S. PATENT DOCUMENTS

| | | |
|---|---|---|
| 3,499,222 A | 3/1970 | Linkow et al. |
| 3,752,203 A | 8/1973 | Hill, Jr. |
| 4,011,602 A | 3/1977 | Rybicki et al. |
| 4,085,744 A | 4/1978 | Lewis et al. |
| 4,179,905 A | 12/1979 | Schultenkamper |
| 4,289,124 A | 9/1981 | Zickel |
| 4,404,967 A | 9/1983 | Bacal et al. |
| 4,411,259 A | 10/1983 | Drummond |
| 4,611,580 A | 9/1986 | Wu |
| 4,611,581 A | 9/1986 | Steffee |
| 4,611,582 A | 9/1986 | Duff |
| 4,641,636 A | 2/1987 | Cotrel |
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |
| 4,743,260 A | 5/1988 | Burton |
| 4,759,769 A | 7/1988 | Hedman et al. |
| 4,763,644 A | 8/1988 | Webb |
| 4,771,767 A | 9/1988 | Steffee |
| 4,773,402 A | 9/1988 | Asher et al. |
| 4,805,602 A | 2/1989 | Puno et al. |
| 4,815,453 A | 3/1989 | Cotrel |
| 4,887,595 A | 12/1989 | Heinig et al. |
| 4,913,134 A | 4/1990 | Luque |
| 4,950,269 A | 8/1990 | Gaines, Jr. |
| 4,957,495 A | 9/1990 | Kluger |
| 5,002,542 A | 3/1991 | Frigg |
| 5,005,562 A | 4/1991 | Cotrel |
| 5,010,879 A | 4/1991 | Moriya et al. |
| 5,024,213 A | 6/1991 | Asher et al. |
| 5,030,220 A | 7/1991 | Howland |
| 5,067,955 A | 11/1991 | Cotrel |
| 5,084,049 A | 1/1992 | Asher et al. |
| 5,092,866 A | 3/1992 | Breard |
| 5,092,893 A | 3/1992 | Smith |
| 5,102,412 A | 4/1992 | Rogozinski |
| 5,113,685 A | 5/1992 | Asher et al. |
| 5,116,334 A | 5/1992 | Cozad et al. |
| 5,120,171 A | 6/1992 | Lasner |
| 5,127,912 A | 7/1992 | Ray et al. |
| 5,129,899 A * | 7/1992 | Small et al. ............... 606/290 |
| 5,129,900 A | 7/1992 | Asher et al. |
| 5,133,716 A | 7/1992 | Plaza |
| 5,147,359 A | 9/1992 | Cozad et al. |
| 5,147,360 A | 9/1992 | Dubousset |
| 5,154,718 A | 10/1992 | Cozad et al. |
| 5,176,678 A | 1/1993 | Tsou |
| 5,176,680 A | 1/1993 | Vignaud et al. |
| 5,190,543 A | 3/1993 | Schlapfer |
| 5,207,678 A | 5/1993 | Harms et al. |
| 5,234,431 A | 8/1993 | Keller |
| 5,242,443 A | 9/1993 | Kambin |
| 5,261,907 A | 11/1993 | Vignaud et al. |
| 5,261,913 A | 11/1993 | Marnay |
| 5,275,600 A | 1/1994 | Allard et al. |
| 5,282,801 A | 2/1994 | Sherman |
| 5,282,863 A | 2/1994 | Burton |
| 5,304,177 A | 4/1994 | Pennig |
| 5,306,275 A | 4/1994 | Bryan |
| 5,312,405 A | 5/1994 | Korotko et al. |
| 5,330,473 A | 7/1994 | Howland |
| 5,334,203 A | 8/1994 | Wagner |
| 5,360,431 A | 11/1994 | Puno et al. |
| 5,366,455 A * | 11/1994 | Dove et al. ............... 606/61 |
| 5,368,594 A | 11/1994 | Martin et al. |
| 5,387,213 A | 2/1995 | Breard et al. |
| 5,395,370 A | 3/1995 | Muller et al. |
| 5,397,363 A * | 3/1995 | Gelbard ............... 606/61 |
| 5,403,316 A | 4/1995 | Ashman |
| 5,415,661 A | 5/1995 | Holmes |
| 5,419,522 A | 5/1995 | Luecke et al. |
| 5,423,818 A | 6/1995 | Van Hoeck et al. |
| 5,437,671 A | 8/1995 | Lozier et al. |
| 5,439,463 A | 8/1995 | Lin |
| 5,454,812 A | 10/1995 | Lin |
| 5,470,333 A | 11/1995 | Ray |
| 5,474,086 A | 12/1995 | McCormick et al. |
| 5,476,462 A | 12/1995 | Allard et al. |
| 5,487,742 A | 1/1996 | Cotrel |
| 5,496,321 A | 3/1996 | Puno et al. |
| 5,498,263 A | 3/1996 | DiNello et al. |
| 5,514,132 A | 5/1996 | Csernatony et al. |
| 5,522,816 A * | 6/1996 | Dinello et al. ............... 606/61 |
| 5,527,314 A | 6/1996 | Brumfield et al. |
| 5,531,745 A | 7/1996 | Ray |
| 5,534,002 A | 7/1996 | Brumfield et al. |
| 5,540,688 A | 7/1996 | Navas |
| 5,549,607 A | 8/1996 | Olson et al. |
| 5,556,431 A | 9/1996 | Buttner-Janz |
| 5,562,662 A | 10/1996 | Brumfield et al. |
| 5,562,663 A | 10/1996 | Wisnewski et al. |
| 5,562,737 A | 10/1996 | Graf |
| 5,571,191 A | 11/1996 | Fitz |
| 5,582,612 A | 12/1996 | Lin |
| 5,584,831 A | 12/1996 | McKay |
| 5,586,983 A | 12/1996 | Sanders et al. |
| 5,591,165 A | 1/1997 | Jackson |
| 5,601,552 A | 2/1997 | Cotrel |
| 5,609,592 A | 3/1997 | Brumfield et al. |
| 5,616,142 A | 4/1997 | Yuan et al. |
| 5,620,444 A | 4/1997 | Assaker |
| 5,624,442 A | 4/1997 | Mellinger et al. |
| 5,630,816 A | 5/1997 | Kambin |
| 5,651,789 A | 7/1997 | Cotrel |
| 5,662,853 A | 9/1997 | Hattori et al. |
| 5,667,506 A | 9/1997 | Sutterlin |
| 5,667,507 A | 9/1997 | Corin et al. |
| 5,669,910 A | 9/1997 | Korhonen et al. |
| 5,672,175 A | 9/1997 | Martin |
| 5,676,703 A | 10/1997 | Gelbard |
| 5,683,393 A | 11/1997 | Ralph |
| 5,688,272 A * | 11/1997 | Montague et al. ............ 606/252 |
| 5,700,292 A | 12/1997 | Margulies |
| 5,704,936 A | 1/1998 | Mazel |
| 5,707,372 A | 1/1998 | Errico et al. |
| 5,709,684 A | 1/1998 | Errico et al. |
| 5,709,685 A | 1/1998 | Dombrowski et al. |
| 5,716,355 A | 2/1998 | Jackson et al. |
| 5,743,907 A | 4/1998 | Asher et al. |
| 5,743,911 A | 4/1998 | Cotrel |
| 5,752,955 A | 5/1998 | Errico |
| 5,776,135 A | 7/1998 | Errico et al. |
| 5,876,403 A | 3/1999 | Shitoto et al. |
| 5,885,284 A | 3/1999 | Errico et al. |
| 5,899,903 A | 5/1999 | Cotrel |
| RE36,221 E | 6/1999 | Breard et al. |
| 5,928,232 A | 7/1999 | Howland et al. |
| 5,937,363 A | 8/1999 | Saidi et al. |
| 5,947,966 A | 9/1999 | Drewry et al. |
| 5,961,516 A | 10/1999 | Graf |
| 5,980,521 A | 11/1999 | Montague et al. |
| 5,980,523 A | 11/1999 | Jackson |
| 5,989,250 A | 11/1999 | Wagner et al. |
| 5,989,251 A | 11/1999 | Nichols |
| 6,063,089 A | 5/2000 | Errico |
| RE36,758 E | 6/2000 | Fitz |
| 6,083,226 A | 7/2000 | Fiz |
| 6,110,173 A | 8/2000 | Thomas, Jr. |
| 6,113,600 A | 9/2000 | Drummond et al. |
| 6,126,660 A | 10/2000 | Dietz |
| 6,132,464 A | 10/2000 | Martin |

| | | | | | | |
|---|---|---|---|---|---|---|
| 6,136,003 | A | 10/2000 | Hoeck et al. | 2004/0006342 A1 | 1/2004 | Altarac et al. |
| 6,139,548 | A | 10/2000 | Errico | 2004/0006391 A1 | 1/2004 | Reiley |
| 6,171,311 | B1 | 1/2001 | Richelsoph | 2004/0039385 A1 | 2/2004 | Mazda |
| 6,217,578 | B1 | 4/2001 | Crozet et al. | 2004/0049188 A1 | 3/2004 | Slivka et al. |
| 6,234,705 | B1 | 5/2001 | Troxell | 2004/0049189 A1 | 3/2004 | Le Couedic et al. |
| 6,238,396 | B1 | 5/2001 | Lombardo | 2004/0049190 A1 | 3/2004 | Biedermann et al. |
| 6,264,658 | B1 | 7/2001 | Lee et al. | 2004/0049272 A1 | 3/2004 | Reiley |
| 6,267,764 | B1 | 7/2001 | Elberg | 2004/0049273 A1 | 3/2004 | Reiley |
| 6,273,888 | B1 | 8/2001 | Justis | 2004/0049274 A1 | 3/2004 | Reiley |
| 6,283,967 | B1 | 9/2001 | Troxell et al. | 2004/0049275 A1 | 3/2004 | Reiley |
| 6,287,309 | B1 | 9/2001 | Baccelli et al. | 2004/0049276 A1 | 3/2004 | Reiley |
| 6,302,882 | B1 | 10/2001 | Lin et al. | 2004/0049277 A1 | 3/2004 | Reiley |
| 6,315,779 | B1 | 11/2001 | Morrison et al. | 2004/0049278 A1 | 3/2004 | Reiley |
| 6,328,741 | B1 | 12/2001 | Richelsoph | 2004/0049281 A1 | 3/2004 | Reiley |
| 6,355,038 | B1 * | 3/2002 | Pisharodi ................ 606/61 | 2004/0073215 A1 | 4/2004 | Carli |
| 6,402,751 | B1 | 6/2002 | Hoeck | 2004/0087949 A1 * | 5/2004 | Bono et al. ................ 606/61 |
| 6,413,257 | B1 | 7/2002 | Lin et al. | 2004/0111154 A1 | 6/2004 | Reiley |
| 6,419,703 | B1 | 7/2002 | Fallin | 2004/0116927 A1 | 6/2004 | Graf |
| 6,432,108 | B1 | 8/2002 | Burgess | 2004/0116928 A1 | 6/2004 | Young et al. |
| 6,440,169 | B1 | 8/2002 | Elberg et al. | 2004/0133203 A1 | 7/2004 | Young et al. |
| 6,524,310 | B1 | 2/2003 | Lombardo et al. | 2004/0143264 A1 | 7/2004 | McAfee |
| 6,551,318 | B1 | 4/2003 | Stahurski | 2004/0186474 A1 * | 9/2004 | Matthis et al. ............. 606/61 |
| 6,554,831 | B1 | 4/2003 | Rivard et al. | 2004/0186475 A1 | 9/2004 | Falahee |
| 6,554,832 | B2 | 4/2003 | Shluzas | 2004/0236329 A1 | 11/2004 | Panjabi |
| 6,565,605 | B2 | 5/2003 | Goble | 2005/0033431 A1 | 2/2005 | Gordon et al. |
| 6,579,319 | B2 | 6/2003 | Goble | 2005/0033432 A1 | 2/2005 | Gordon et al. |
| 6,602,253 | B2 | 8/2003 | Richelsoph et al. | 2005/0033439 A1 | 2/2005 | Gordon et al. |
| 6,610,091 | B1 | 8/2003 | Reiley | 2005/0090821 A1 | 4/2005 | Berrevoets et al. |
| 6,616,668 | B2 | 9/2003 | Altarac et al. | 2005/0101954 A1 | 5/2005 | Simonson |
| 6,616,669 | B2 | 9/2003 | Ogilvie et al. | 2005/0101956 A1 | 5/2005 | Simonson |
| 6,641,583 | B2 | 11/2003 | Shluzas et al. | 2005/0102028 A1 | 5/2005 | Arnin et al. |
| 6,645,207 | B2 | 11/2003 | Dixon | 2005/0113927 A1 | 5/2005 | Malek |
| 6,669,729 | B2 | 12/2003 | Chin | 2005/0119657 A1 | 6/2005 | Goldsmith |
| 6,673,073 | B1 | 1/2004 | Schafer | 2005/0228326 A1 | 10/2005 | Kalfas et al. |
| 6,689,133 | B2 | 2/2004 | Morrison | 2005/0228377 A1 | 10/2005 | Chao et al. |
| 6,736,817 | B2 | 5/2004 | Troxell | 2006/0058789 A1 | 3/2006 | Kim et al. |
| 6,752,807 | B2 | 6/2004 | Lin | 2006/0142759 A1 | 6/2006 | Arnin et al. |
| 6,761,721 | B2 | 7/2004 | Burgess et al. | 2006/0241757 A1 | 10/2006 | Anderson |
| 6,811,567 | B2 | 11/2004 | Reiley | 2007/0043356 A1 | 2/2007 | Timm et al. |
| 6,887,241 | B1 | 5/2005 | McBride et al. | 2007/0049936 A1 | 3/2007 | Colleran et al. |
| 6,958,066 | B2 | 10/2005 | Richelsoph et al. | 2007/0073396 A1 | 3/2007 | Arnin |
| 7,011,685 | B2 | 3/2006 | Arnin et al. | | | |
| 2002/0007183 | A1 | 1/2002 | Lee et al. | | | |
| 2002/0052603 | A1 | 5/2002 | Nichols et al. | | | |
| 2002/0065557 | A1 | 5/2002 | Goble et al. | | | |
| 2002/0072800 | A1 | 6/2002 | Goble et al. | | | |
| 2002/0095154 | A1 | 7/2002 | Atkinson et al. | | | |
| 2002/0111625 | A1 | 8/2002 | Richelsoph et al. | | | |
| 2002/0123806 | A1 | 9/2002 | Reiley | | | |
| 2002/0133155 | A1 | 9/2002 | Ferree | | | |
| 2002/0138077 | A1 | 9/2002 | Ferree | | | |
| 2002/0143330 | A1 | 10/2002 | Shluzas | | | |
| 2002/0169448 | A1 | 11/2002 | Vanacker | | | |
| 2003/0004572 | A1 | 1/2003 | Goble et al. | | | |
| 2003/0018334 | A1 | 1/2003 | Richelsoph et al. | | | |
| 2003/0023244 | A1 | 1/2003 | Richelsoph et al. | | | |
| 2003/0028192 | A1 | 2/2003 | Schar et al. | | | |
| 2003/0028250 | A1 | 2/2003 | Reiley et al. | | | |
| 2003/0045874 | A1 | 3/2003 | Thomas | | | |
| 2003/0055427 | A1 | 3/2003 | Graf | | | |
| 2003/0083657 | A1 | 5/2003 | Drewry | | | |
| 2003/0109880 | A1 | 6/2003 | Shirado et al. | | | |
| 2003/0114853 | A1 | 6/2003 | Burgess et al. | | | |
| 2003/0135277 | A1 | 7/2003 | Bryan et al. | | | |
| 2003/0153912 | A1 | 8/2003 | Graf | | | |
| 2003/0153917 | A1 | 8/2003 | Richelsoph et al. | | | |
| 2003/0171749 | A1 | 9/2003 | Le Couedic et al. | | | |
| 2003/0171750 | A1 | 9/2003 | Chin | | | |
| 2003/0191470 | A1 | 10/2003 | Ritland | | | |
| 2003/0191532 | A1 | 10/2003 | Goble et al. | | | |
| 2003/0220642 | A1 | 11/2003 | Freudiger | | | |
| 2003/0220643 | A1 | 11/2003 | Ferree | | | |
| 2004/0002708 | A1 | 1/2004 | Ritland | | | |

FOREIGN PATENT DOCUMENTS

| | | |
|---|---|---|
| DE | 3219575 | 12/1983 |
| DE | 3639810 | 5/1988 |
| DE | 4330837 | 3/1995 |
| EP | 0128058 | 12/1984 |
| EP | 0242708 | 10/1987 |
| EP | 0669109 | 2/1994 |
| EP | 0820722 | 1/1998 |
| EP | 0878170 | 11/1998 |
| EP | 0956829 | 11/1999 |
| EP | 1295566 | 3/2003 |
| FR | 2615095 | 11/1988 |
| FR | 2645427 | 10/1990 |
| FR | 2697743 | 5/1994 |
| FR | 2714590 | 7/1995 |
| FR | 2615095 | 11/1998 |
| FR | 2624720 | 6/1999 |
| FR | 2813782 | 3/2002 |
| FR | 2816195 | 5/2002 |
| FR | 2795622 | 1/2005 |
| GB | 167228 | 7/1921 |
| GB | 2173104 | 10/1986 |
| GB | 2208476 | 4/1989 |
| JP | 11-244299 | 9/1999 |
| JP | 2000-033091 | 2/2000 |
| RU | 1823791 | 6/1993 |
| SU | 286136 | 11/1970 |
| WO | WO-87/00160 | 1/1987 |
| WO | WO-90/04948 | 5/1990 |
| WO | WO-91/16020 | 10/1991 |

| | | |
|---|---|---|
| WO | WO-95/13754 | 5/1995 |
| WO | 9909903 | 3/1999 |
| WO | WO-9909903 | 3/1999 |
| WO | WO-00/57801 | 10/2000 |
| WO | WO-00/59387 | 10/2000 |
| WO | WO-01/01872 | 1/2001 |
| WO | WO-01/24718 | 4/2001 |
| WO | WO-01/45576 | 6/2001 |
| WO | WO-02/17803 | 3/2002 |
| WO | WO-02/30307 | 4/2002 |
| WO | WO-02/43603 | 6/2002 |
| WO | WO-02/102259 | 12/2002 |
| WO | WO-03/007828 | 1/2003 |
| WO | WO-03/009737 | 2/2003 |
| WO | WO-2004/024011 | 3/2004 |
| WO | WO-2004/034916 | 4/2004 |
| WO | WO 01/47425 A1 * | 7/2007 |

OTHER PUBLICATIONS

Carson et al., "Internal Forces and Moments in Transpecular Spine Instrumentation", SPINE, vol. 15, No. 9, pp. 893-901.

Martin H. Krag, "Biomechanics of Thorocolumbar Spinal Fixation," SPINE, vol. 16, No. 3, Supplement, pp. S84-S99 (1991).

Lim, et al., "Biomechanics of Transfixation in Pedicle Screw Instrumentation", SPINE, vol. 21, No. 19, pp. 2224-2229, 1996.

Betz, Randall R. et al., DePuy AcroMed Brochure, "Fronterior Anterior Deformity System," Surgical Technique, 21 pages, Aug. 2002.

DePuy AcroMed, "CrossOver CrossConnector" brochure, Apr. 2003.

Dick et al., "Mechanical Evaluation of Cross-Link Designs in Rigid Pedicle Screw Systems", SPINE, vol. 22, No. 4, pp. 370-375, 1997.

Kaneda, Kiyoshi et al., DePuy AcroMed Brochure "Kaneda SR Anterior Spinal System," Surgical Technique, pp. 1-11, 1999.

"Ovation™ Polyaxial System" by Osteotech Inc. (author unknown), description downloaded from http://www.osteotech.com/prodpoly2.htm; pp. 1-6; (Oct. 28, 2003).

DePuy AcroMed, "Modular Cross Connector (MCC)" brochure, 2000.

International Search Report issued for PCT/US06/31000; mailing date Mar. 20, 2008; 4 pages.

Carson et al., "Internal Forces and Moments in Transpecular Spine Instrumentation", SPINE, vol. 15, No. 9, pp. 893-901 (1999).

Hitodo, H., "Bone Fixing Device," Patent Abstracts of Japan; Sep. 14, 1999, No. 14; Abstract of JP 11244299.

* cited by examiner

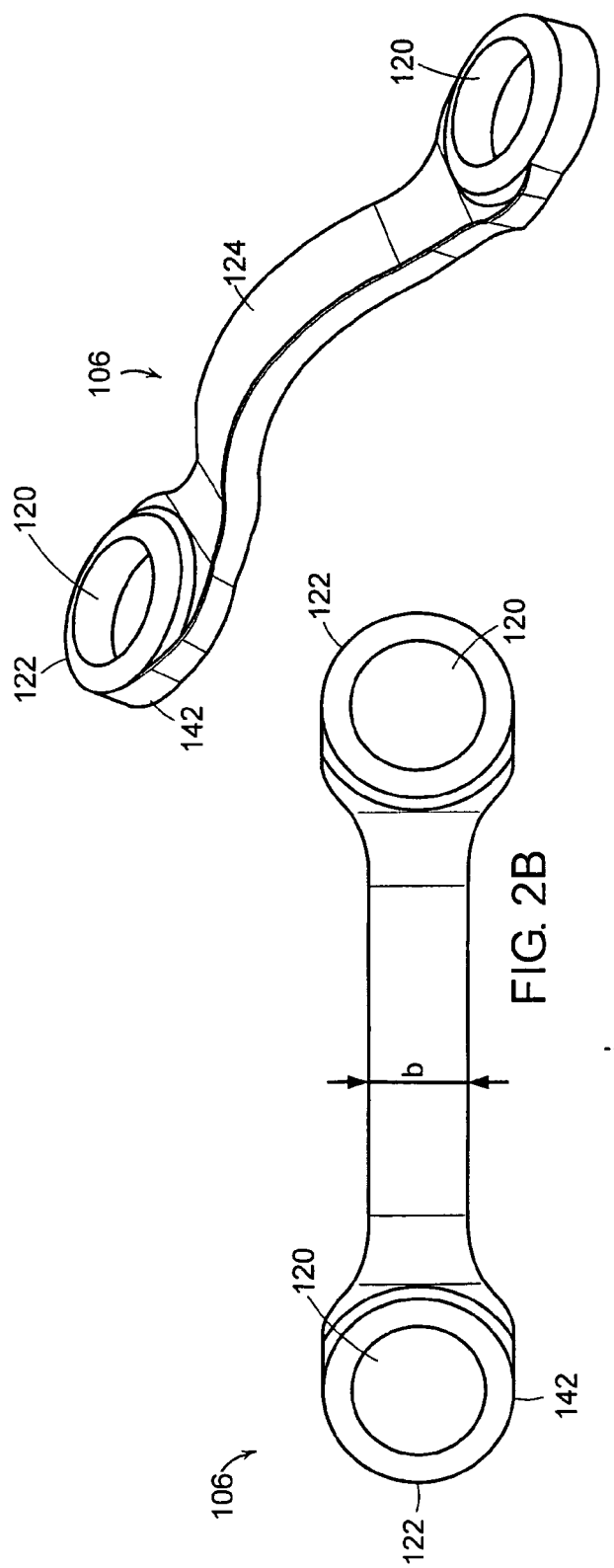

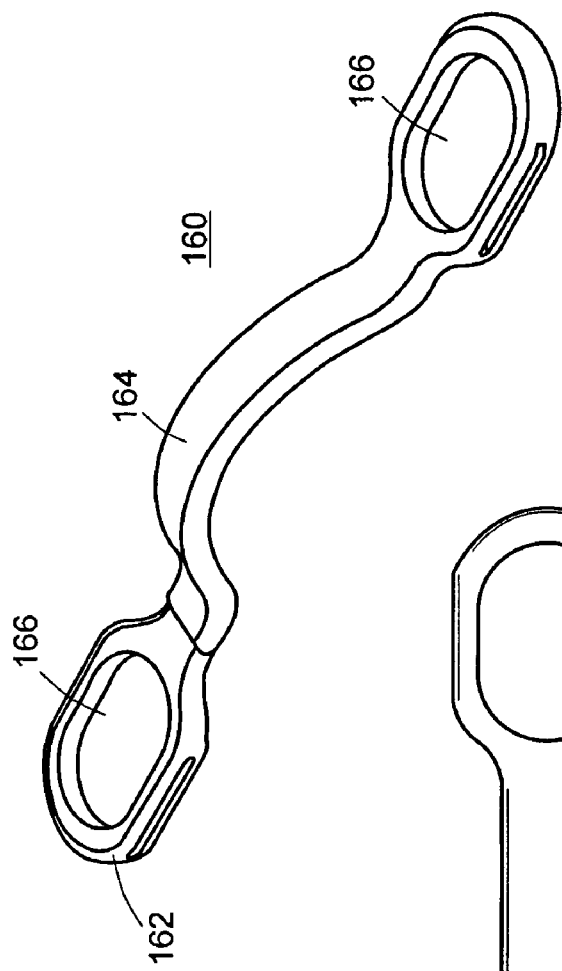
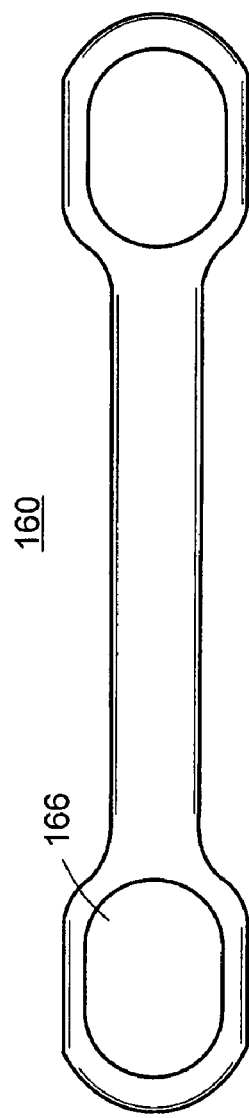
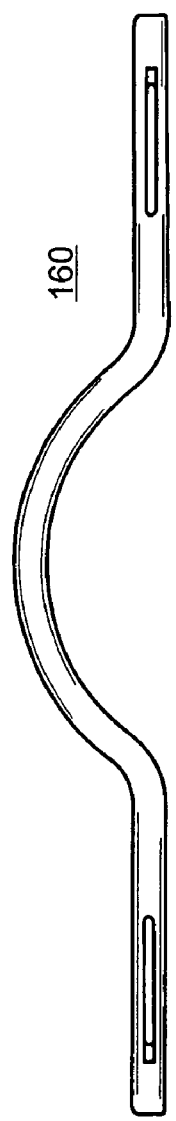
FIG. 11A
FIG. 11B
FIG. 11C

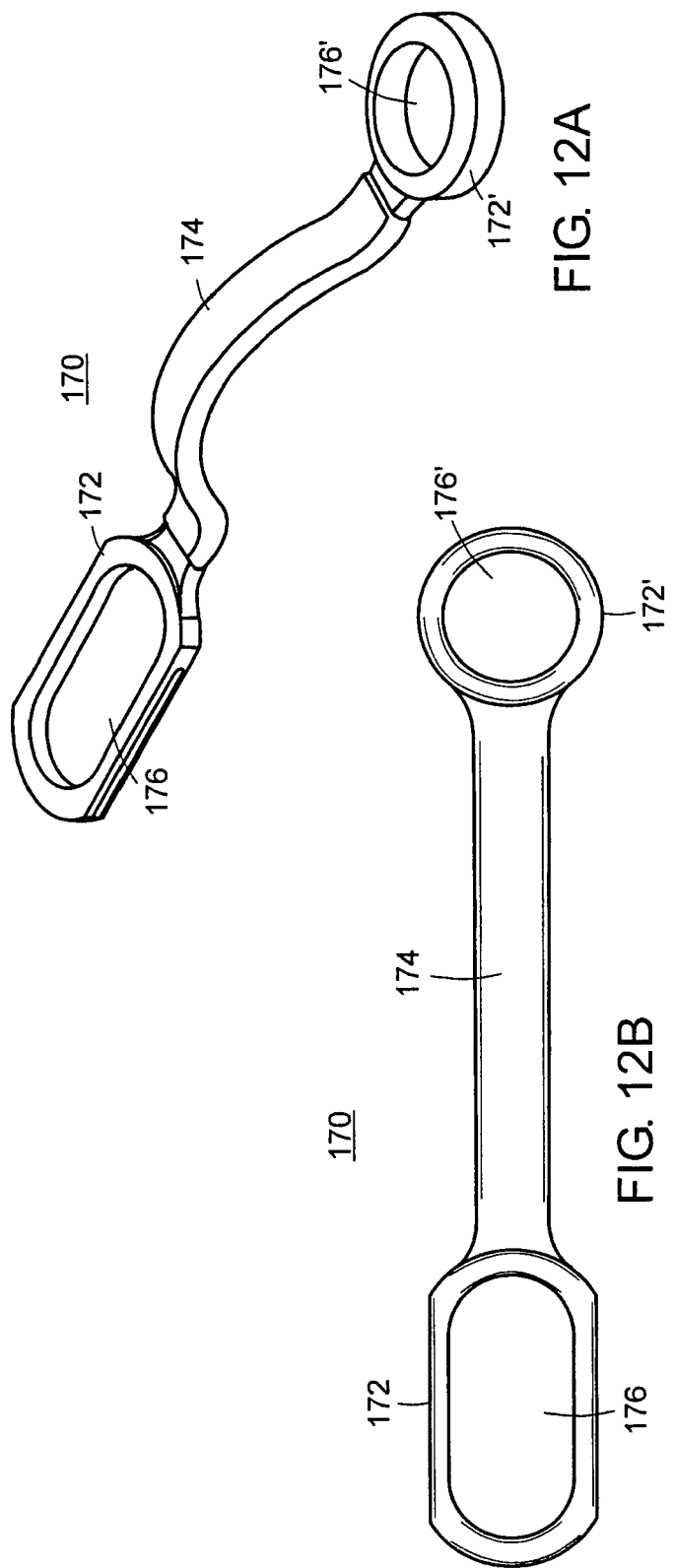

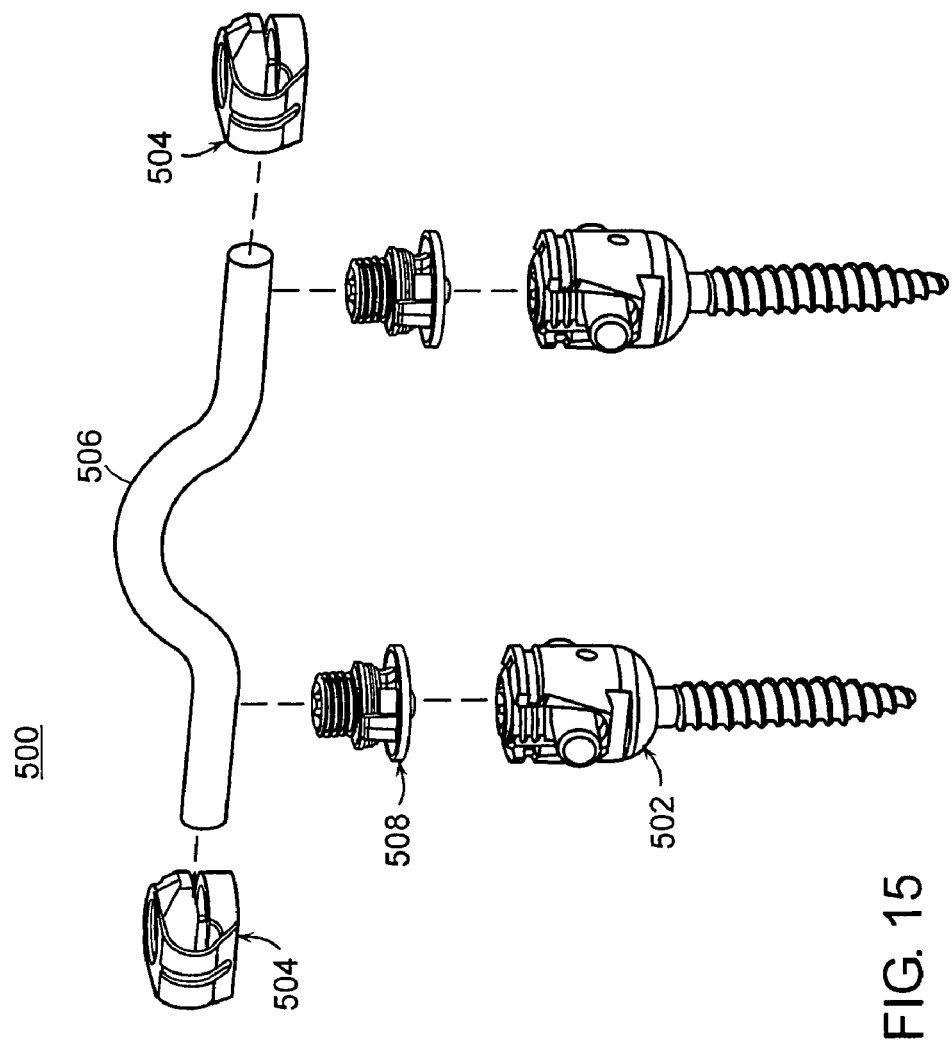
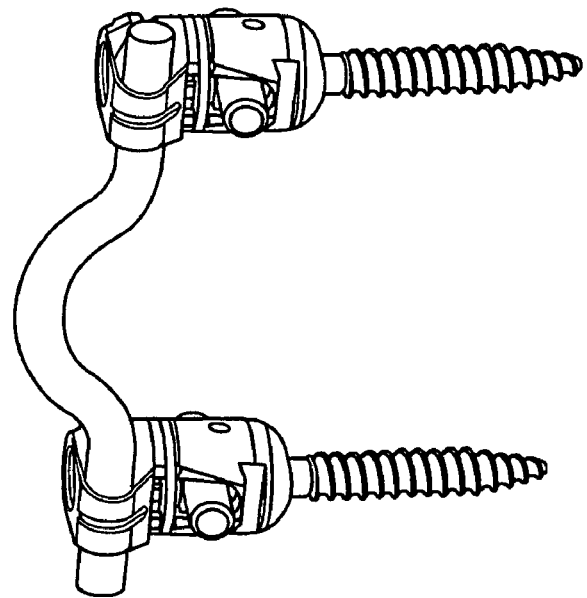
FIG. 15

HEAD-TO-HEAD CONNECTOR SPINAL FIXATION SYSTEM

BACKGROUND OF THE INVENTION

Spinal fixation systems are implanted during a surgical procedure to treat a variety of problems that include correction of congenital spinal deformities, repair of spinal injuries and fusion of vertebra to stabilize degenerative conditions and alleviate chronic lower back pain. It is well known in the correction of spinal deformities to affix a rod or pair of rods longitudinally to the spinal column with a plurality of screws. It is further common to cross link or interconnect the longitudinal rods to provide additional stabilization by using at least one additional member to horizontally bridge the pair of spinal rods. Devices such as these commonly consist of a brace or connector for providing the desired lateral support. The connector is fastened to each of the spinal rods by clamps or other means located on each end of the connector.

Usually, a surgeon first attaches the screws to the spine in appropriate positions, then attaches each screw to a spinal rod and determines where to place the connectors. However, a curvature of the spine and limited available space sometimes results in such an alignment of the screws that a connector must be skipped at a position where the surgeon would place it otherwise. This can happen when linear distance between two adjacent screws is insufficient for fastening a connector to the rod.

Therefore, a need exists for a spinal fixation system that overcomes or minimizes the above-referenced problems.

SUMMARY OF THE INVENTION

The present invention relates to a spinal fixation assembly and an orthopedic implantation device for use in spinal fixation, comprising at least two bone anchors and a connecting plate for connecting the bone anchors.

In one embodiment, the present invention is a spinal fixation system, comprising at least two bone anchors; a rod connecting the bone anchors; and a connecting plate extending from a proximal surface of at least one of the bone anchors.

In another embodiment, the present invention is a connecting plate for connection to at least one bone anchor, comprising an end portion defining an opening, the opening having a distal bearing surface and a proximal bearing surface, the end portion defining at least one plane; and a spanning portion extending from the end portion, at least a portion of the spanning portion being offset from the at least one plane defined by the end portion.

In another embodiment, the present invention is a bone anchor for use with an orthopedic device comprising a distal portion for engaging a bone and a rod-receiving portion, connected to the distal portion, for engaging a rod, wherein the rod-receiving portion defines a convex proximal bearing surface.

In another embodiment, the present invention is a spinal fixation system, comprising a first set of at least two bone anchors; a second set of at least one bone anchor; a fixation element connecting the bone anchors of the first set; and a connecting plate connecting a bone anchor of the first set with a bone anchor of the second set.

In another embodiment, the present invention is a method of fixing vertebrae relative to each other, comprising the steps of implanting a first bone anchor and a second bone anchor in a first vertebra and a second vertebra, respectively; connecting the first and second bone anchors with a fixation element and coupling one end of a connecting plate to a proximal bearing surface of at least a portion of the first bone anchor.

In another embodiment, the present invention is a method of decompression of the spinal canal, the method comprising dissecting a posterior element of a vertebra; positioning the posterior element of the vertebra to expand the spinal canal; and maintaining the position of the posterior element with a connecting plate coupled to a bone anchor fastened to the vertebra.

One advantage of the present invention is that it allows the operating surgeon to select a proper position for a connector independent of local curvature of the spine and the available space along a rod between screws. Another advantage of the invention is that it provides an implantable spinal fixation assembly with a relatively small number of elements, thus resulting in easier implantation and increased reliability. Yet another advantage of the invention is that it prevents splaying of the head of the polyaxial screw of the invention due to a combination of engaged convex and concave surfaces.

BRIEF DESCRIPTION OF THE DRAWINGS

FIG. 2A is a perspective view of one embodiment of a connecting plate of the present invention.

FIG. 2B is a top view of the embodiment of FIG. 2A.

FIG. 2C is a side view of the embodiment of FIG. 2-A.

FIG. 11A is a perspective view of an embodiment of a connecting plate of the present invention.

FIG. 11B is a top view of the embodiment of FIG. 11A.

FIG. 11C is a side view of the embodiment of FIG. 11A.

FIG. 12A is a perspective view of another embodiment of a connecting plate of the present invention.

FIG. 12B is a top view of the embodiment of FIG. 12A.

FIG. 12C is a side view of the embodiment of FIG. 12A.

FIG. 15 is a perspective view of an alternative embodiment of a spinal fixation system of the present invention.

DETAILED DESCRIPTION OF THE INVENTION

Figure 1A:
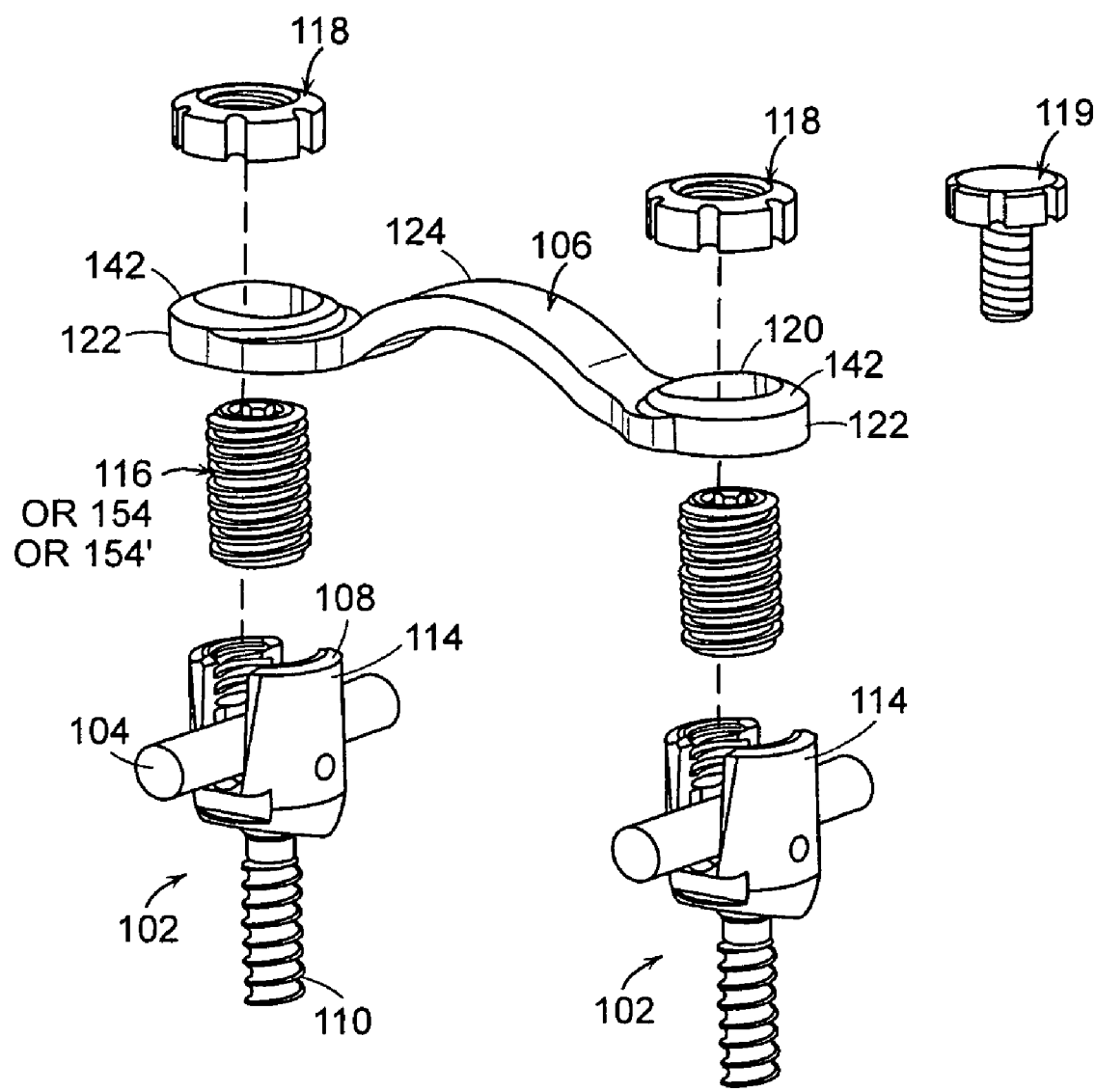
FIG. 1A is a perspective view of one embodiment of a spinal fixation system of the present invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

A spinal fixation assembly of the present invention generally includes one or more bone anchors which are implanted through a portion of a vertebra, for example, the pedicle, lamina, or lateral mass of the vertebra. The bone anchors, described in detail below, may be connected by a spinal fixation element, such as, for example a rod, plate, or cable. The spinal fixation element extends generally along the axis of the spine to fix one or more vertebrae of the spine. One or more connecting plates, described in detail below, can be attached to the bone anchors. These connecting plates can be attached to the bone anchors implanted on opposing sides of the spine, thus providing additional stability to the assembly. In one embodiment, the connecting plate can protect the spinal cord after a full or partial laminectomy. The term "distal", as used in the instant disclosure, means farther from the surgeon, facing into the body; the term "proximal" means closer to the surgeon, facing out of the body.

The term "distal", as used in the instant disclosure, means farther from the surgeon, facing into the body; the term "proximal" means closer to the surgeon, facing out of the body.

Figure 1B:
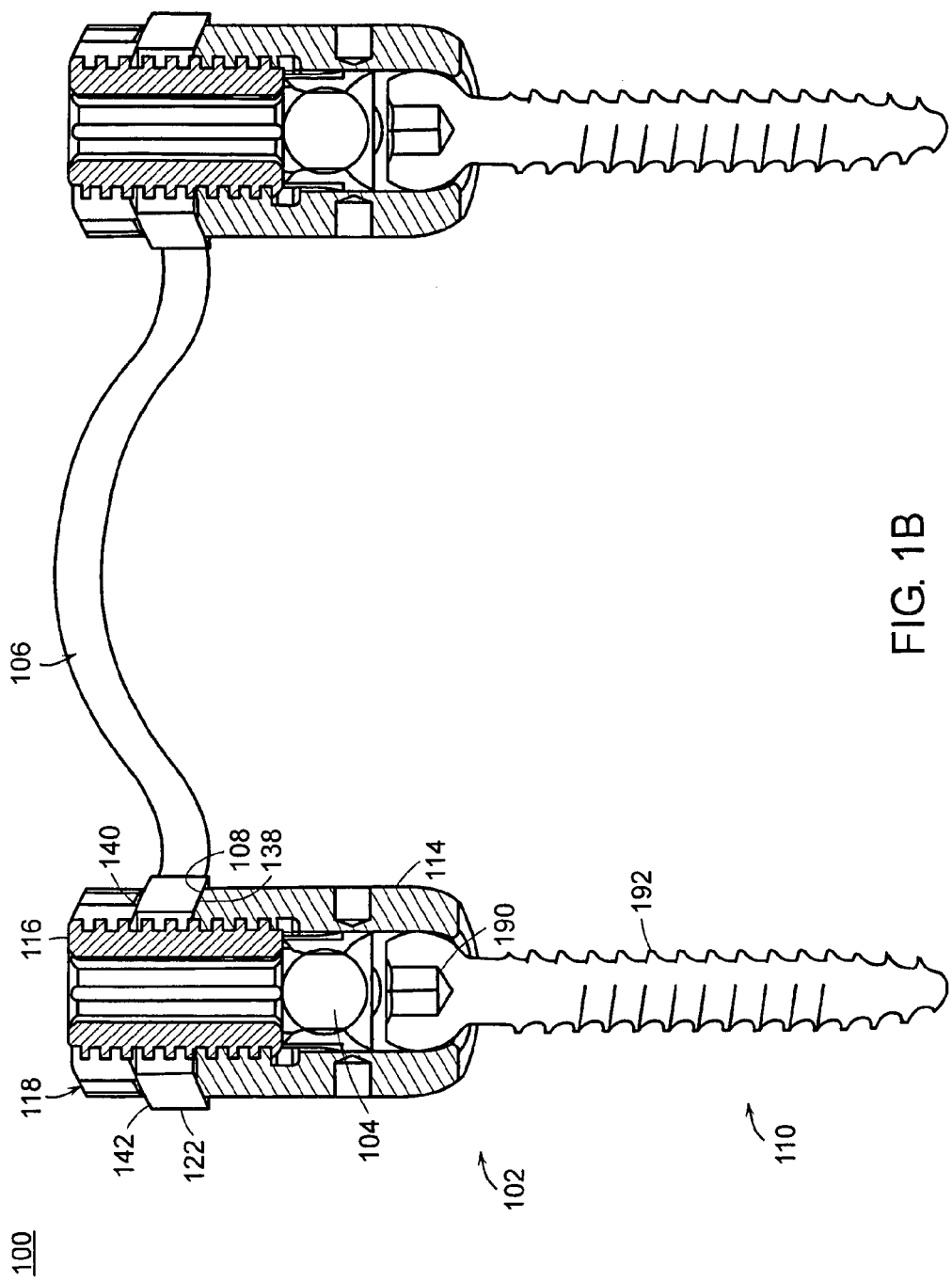
FIG. 1B is a cross-section of the system shown in FIG. 1A.

In one embodiment, a spinal fixation system 100 is shown in FIG. 1A and FIG. 1B. Referring to FIGS. 1A and 1B, the system of the present invention includes at least two bone anchors 102, a spinal fixation element in the form of a rod 104 connecting the bone anchors 102, and connecting plate 106, extending from proximal surface 108 of at least one of bone anchors 102. The bone anchors 102 may be a monoaxial bone screw, a polyaxial bone screw, a bolt, a hook, or any other implant or combination of implants designed to engage bone and connect to a spinal fixation element. In the illustrated embodiments described below, the bone anchors 102 are polyaxial screws, although one of ordinary skill in the art will appreciate that other types of bone anchors may be employed. Each of bone anchors 102 in the exemplary embodiment includes distal portion 110 and rod receiving portion 114.

Spinal fixation system 100 further includes set screw 116 that threadably engages rod receiving portion 114, whereby set screw 116 contacts and fixes rod 104 to bone anchor 102. Although, one of ordinary skill in the art will appreciate that closure mechanisms other than a threaded set screw may be employed to fix the rod 104 to the bone anchor. For example, in other embodiments, a twist-in, non-threaded closure mechanism may be employed.

Spinal fixation system 100 further includes cap 118 or, alternatively, cap 119, that threadably engages set screw 116, whereby cap 118 fixes connecting plate 106 to rod-receiving portion 114 of bone anchor 102.

Figure 3A:
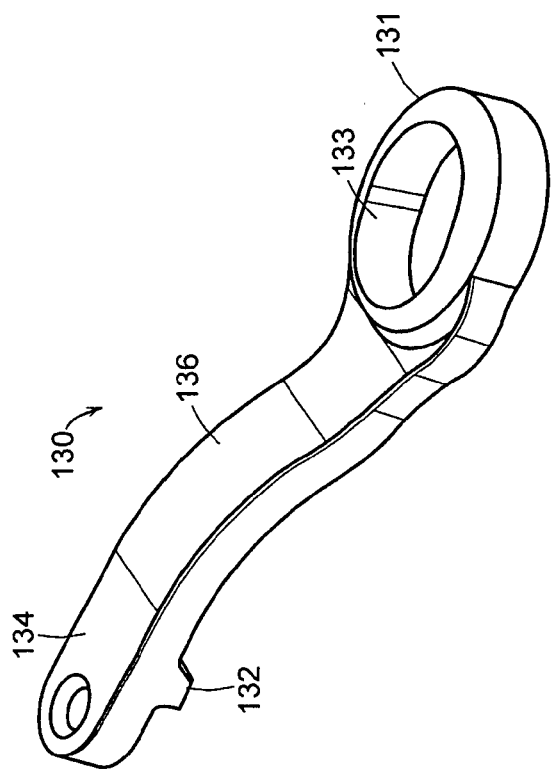
FIG. 3A is a perspective view of another embodiment of a connecting plate of the present invention.

Referring now to FIGS. 1A and 1B and, specifically, to FIGS. 2A, B and C, connecting plate 106 defines opening 120 for receiving at least one bone anchor 102 at end 122 and spanning portion 124 extending from end 122. In one embodiment, set screw 116 or caps 118 or 119 extend through opening 120 when connecting plate 106 is fixed to bone anchor 102. In one embodiment of a connecting plate, shown in FIGS. 3A, B and C, connecting plate 130 includes buttress 132 at distal side 134 of spanning portion 136.

In one embodiment of system 100, there are provided two sets of bone anchors 102. As used herein, a "set" refers to one or more bone anchors, implanted on the same side of the spine, and connected by a rod. Accordingly, in one embodiment, bone anchors of one set are connected by rods 104 and bone anchors of one set are connected to bone anchors of another set by connecting plates 106.

Referring to FIG. 1A-B and FIGS. 2A-C, in one embodiment, connecting plate 106 has distal bearing surface 138 that is domed. Proximal surface 108 of bone anchor 102 mates with connecting plate 106 so that proximal surface 108 bears onto distal surface 138 of connecting plate 106. Distal surface 138 can be spherically or conically domed.

In other embodiments, the bearing surfaces may be flat or may have any other shape sufficient to facilitate coupling of the plate to the bone anchor.

Referring to FIGS. 1 A and B, in one embodiment of system 100, connecting plate 106 is oriented at an angle in a range between about 20° and about 160° relative to rod 104. In another embodiment, connecting plate 106 is oriented at an angle in a range between about 60° and about 120° relative to rod 104.

Referring now to FIGS. 4A-D and FIGS. 5A, B and C, cap 118 or 119 has distal bearing surface 140 that is chamfered or domed. Distal bearing surface 140 of cap 118 or 119 mates with proximal bearing surface 142 of connecting plate 106.

Figure 6:
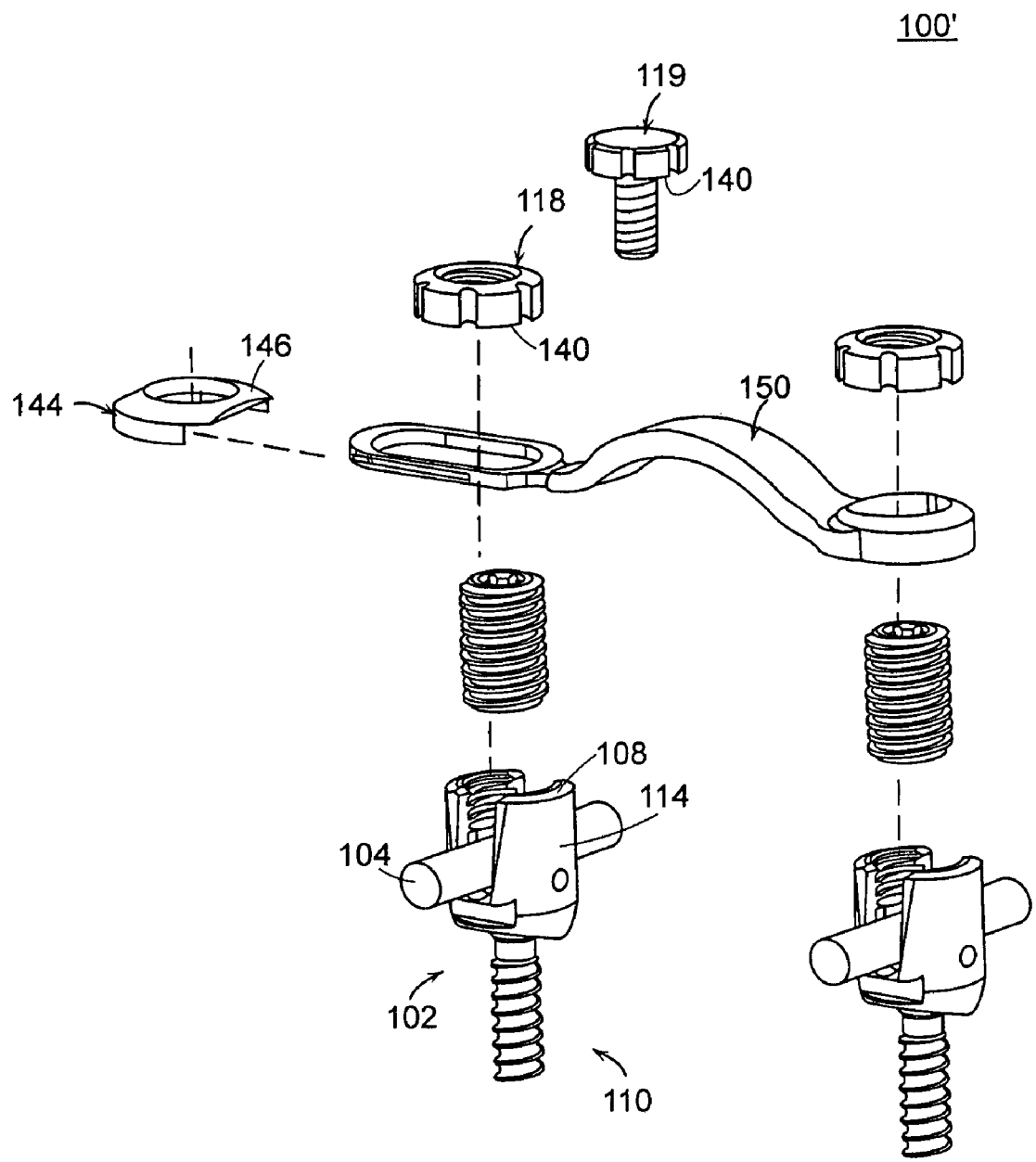
FIG. 6 is a perspective view of an embodiment of a spinal fixation system of the present invention that includes a floating washer.
Figure 7A:
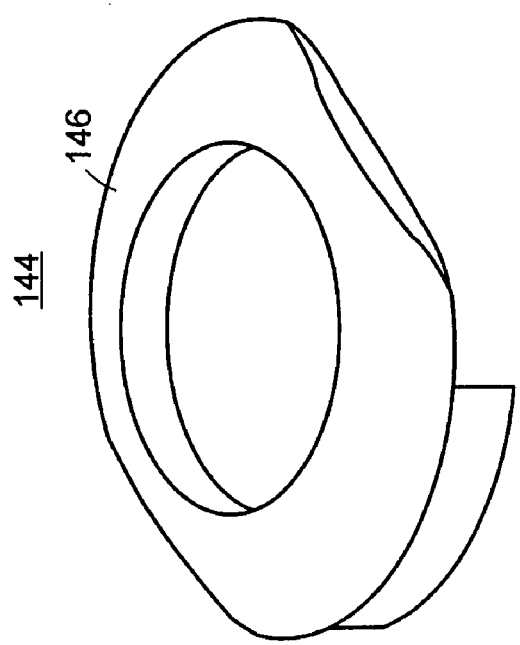
FIG. 7A is a perspective view of the floating washer of the embodiment of FIG. 6.
Figure 7B:
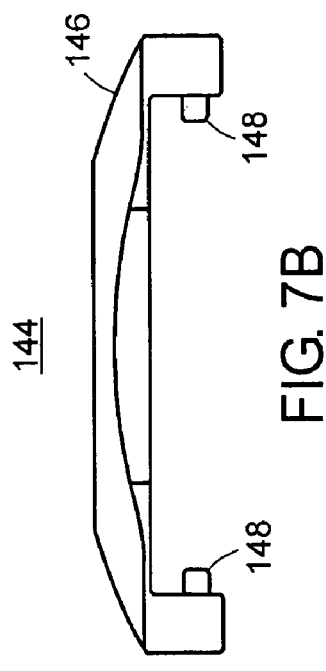
FIG. 7B is a side view of the embodiment of FIG. 7A.
Figure 7C:
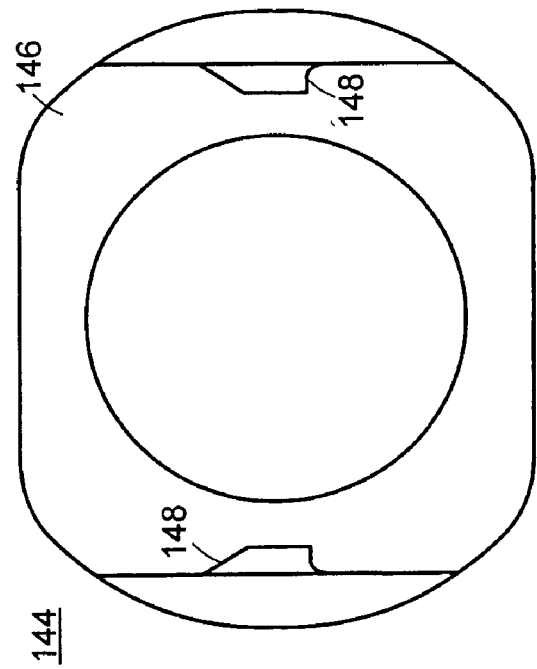
FIG. 7C is a top view of the embodiment of FIG. 7A.
Figure 8A:
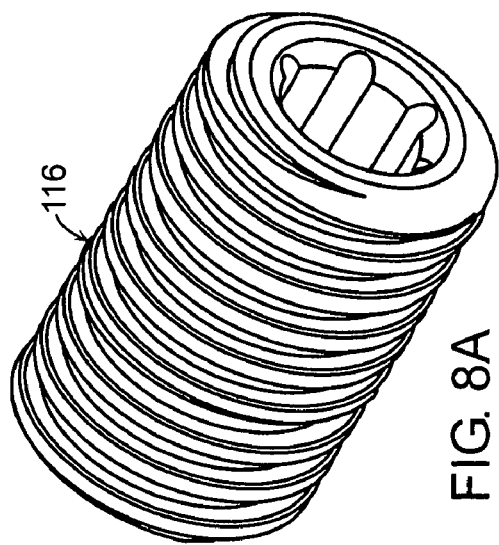
FIG. 8A is a perspective view of an embodiment of a set screw of the spinal fixation system of the present invention.
Figure 8B:
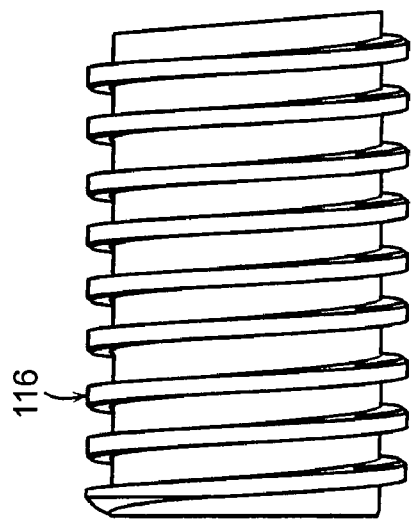
FIG. 8B is a side view of the embodiment of FIG. 8A.
Figure 8C:
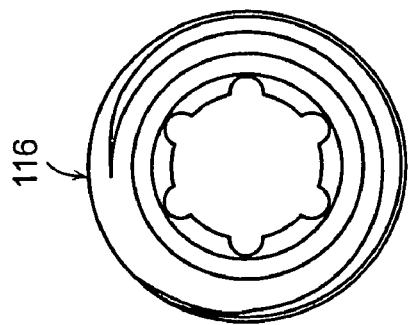
FIG. 8C is a top view of the embodiment of FIG. 8A.
Figure 9A:
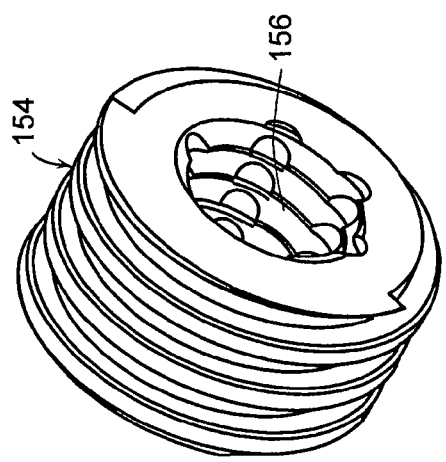
FIG. 9A is a perspective view of another embodiment of a set screw of the spinal fixation system of the present invention.
Figure 9D:
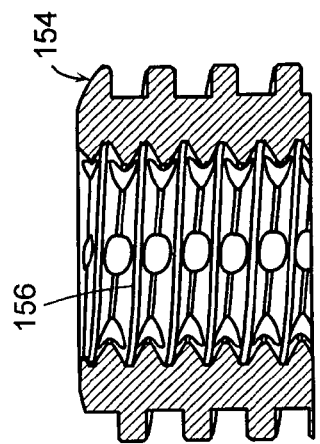
FIG. 9D is a cross-section view of the embodiment of FIG. 9A.
Figure 9C:
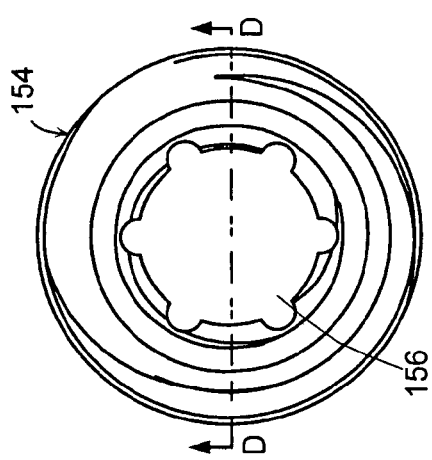
FIG. 9C is a top view of the embodiment of FIG. 9A.
Figure 9B:
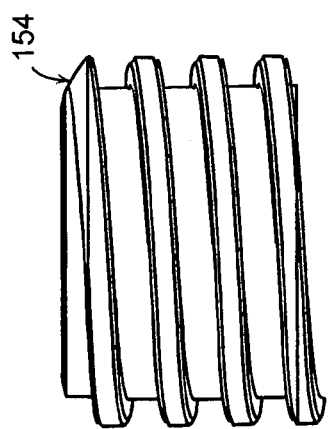
FIG. 9B is a side view of the embodiment of FIG. 9A.
Figure 10A:
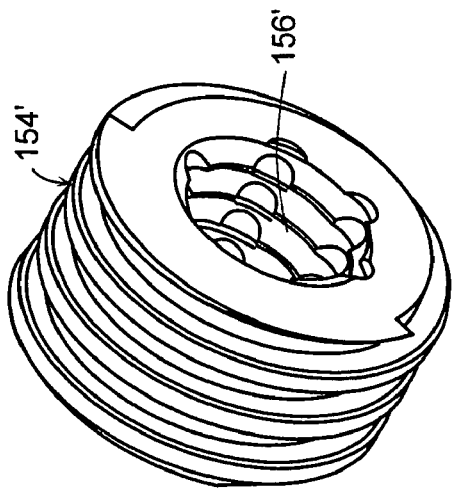
FIG. 10A is a perspective view of another embodiment of a set screw of the spinal fixation system of the present invention.
Figure 10D:
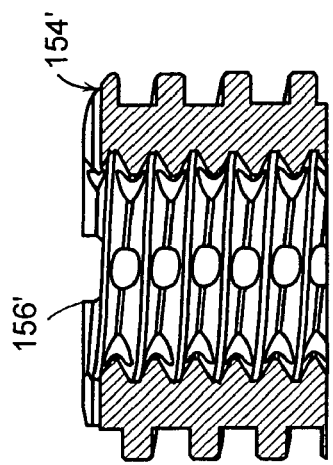
FIG. 10D is a cross-section view of the embodiment of FIG. 10A.
Figure 10C:
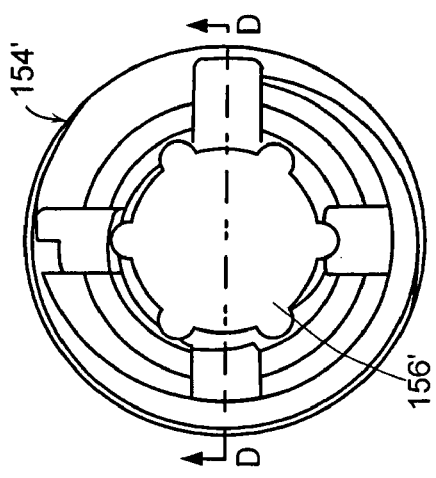
FIG. 10C is a top view of the embodiment of FIG. 10A.
Figure 10B:
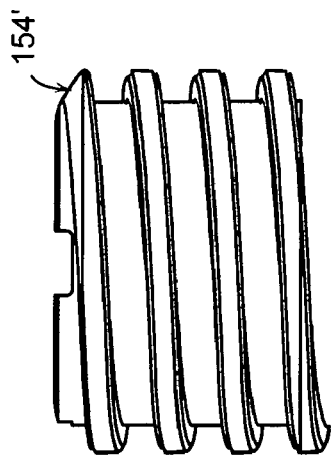
FIG. 10B is a side view of the embodiment of FIG. 10A.

In another embodiment, the spinal fixation system of the invention is system 100' as shown in FIG. 6. Referring to FIG. 6 and, specifically, to FIGS. 7A-C, system 100' of the present invention further includes floating washer 144. Floating washer 144 includes bearing surface 146 that mates with distal bearing surface 140 of cap 118 or 119, and rails 148 that slidably engage connecting plate 150. Connecting plate 150 is fixed to bone anchor 102 by compression between floating washer 144 and bone anchor 102. In one embodiment of system 100', distal bearing surface 140 of cap 118 or 119 is domed.

Referring to FIGS. 4A-D and FIGS. 8A-C, in one embodiment of the invention, cap 118 threadably engages set screw 116 at threaded bore 152 defined by cap 118. In an alternative embodiment, and now referring to FIG. 4 and FIGS. 9A-D and 10A-D, cap 119 threadably engages threaded bore 156 or 156' defined by set screw 154 (FIGS. 9A-D) or 154' (FIGS. 10A-D).

Figure 3B:
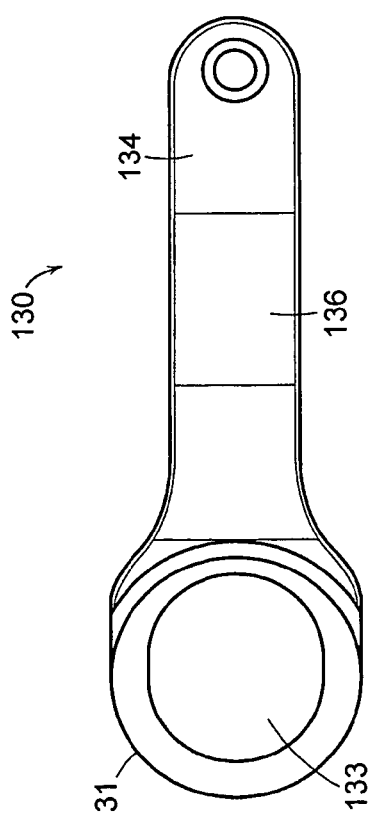
FIG. 3B is a top view of the embodiment of FIG. 3A.
Figure 3C:
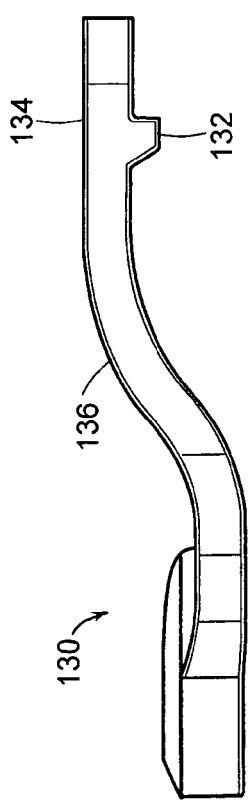
FIG. 3C is a side view of the embodiment of FIG. 3A.
Figure 4A:
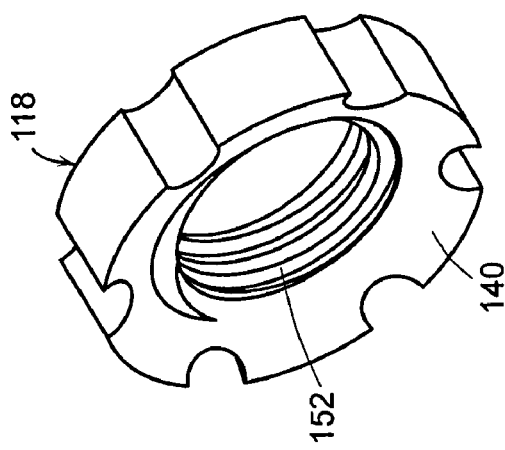
FIG. 4A is a perspective view of an alternative embodiments of a cap of the present invention.
Figure 4B:
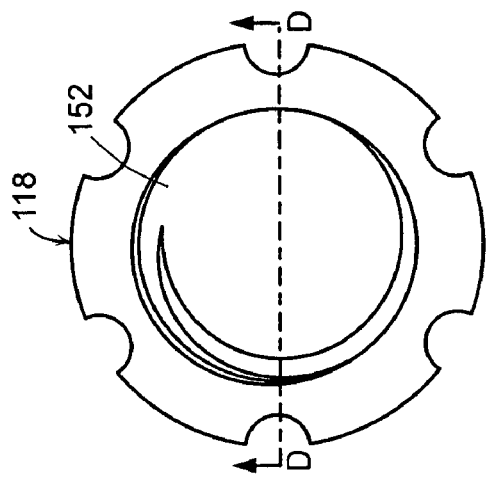
FIG. 4B is a top view of the embodiment of FIG. 4A.
Figure 4C:
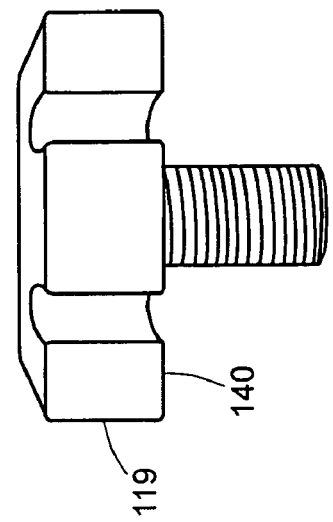
FIG. 4C is a side view of the embodiment of FIG. 4A.
Figure 4D:
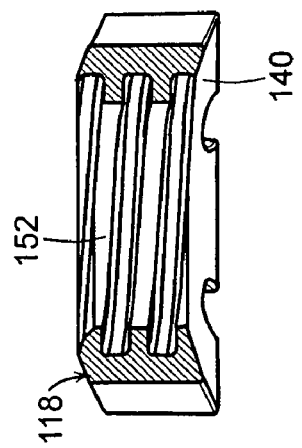
FIG. 4D is a cross-section view of the embodiment of FIG. 4A.
Figure 13A:
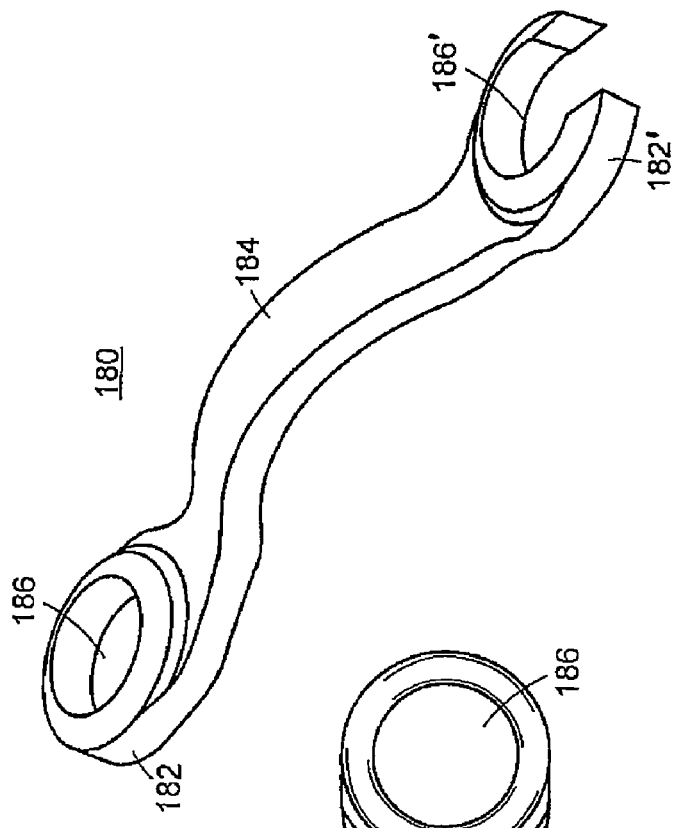
FIG. 13A is a perspective view of another embodiment of a connecting plate of the present invention.
Figure 13B:
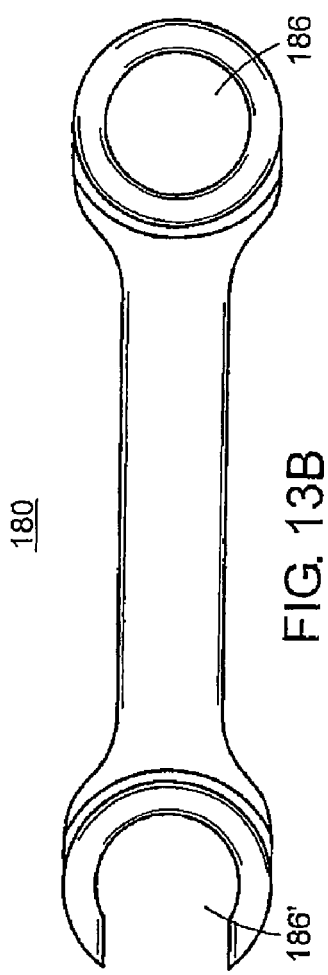
FIG. 13B is a top view of the embodiment of FIG. 13A.
Figure 13C:
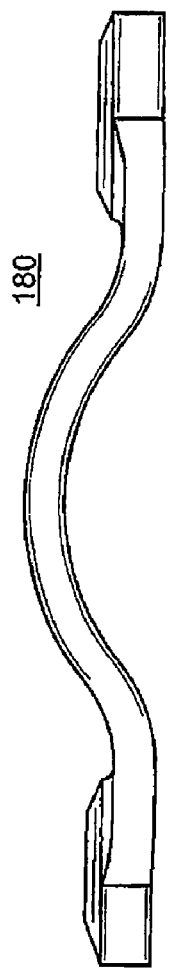
FIG. 13C is a side view of the embodiment of FIG. 13A.

Description of a spanning plate of the invention will now be given with reference to connecting plate 106 as shown in FIGS. 2A-C. It will be understood that any of the alternative embodiments of a connecting plate 106, such as 130 (FIG. 3), 160 (FIG. 11), 170 (FIG. 12) and 180 (FIG. 13), have equivalent elements including at least one end (131 in FIG. 3, 162 in FIG. 11, 172 or 172' in FIG. 12 and 182 or 182' in FIG. 13) defining an opening (133 in FIG. 3, 166 in FIG. 11, 176 or 176' in FIG. 12 and 186 or 186' in FIG. 13) and a spanning portion (136 in FIG. 3, 164 in FIG. 11, 174 in FIG. 12 and 184 in FIG. 13). Description of elements of spanning plate 106 is equivalent to the description of like elements of the alternative embodiments.

Referring to FIGS. 2A-C, connecting plate 106 defines opening 120 at each end 122. During the operation of the system of the present invention, each end 122 is fixed to proximal surface 108 of bone anchor 102 (see FIGS. 1A and 1B). In one embodiment, spanning portion 124 of connecting plate 106 is arcuate, having a radius of curvature in a range of between about 5 mm and about 15 mm. In another embodiment, the radius of curvature is in the range of between about 8 mm and about 12 mm. Openings 120, defined by connecting plate 106, may circular, elliptical, polygonal, or have any other shape suitable for accepting the bone anchor. In one embodiment, shown in FIG. 13, opening 186 defined by connecting plate 184 is open-ended. The spanning portion 124 of the connecting plate 106, in one embodiment, may have a thickness a, as indicated in FIG. 2C (side view) that is less that a width b of the plate, as indicated in FIG. 2B (top view). Such a configuration allows for intraoperative contouring of the plate to accommodate patient anatomy yet also provides geometric stiffness to impart torsional rigidity to the plate and spinal construct. Further referring to FIGS. 2A-C, in one embodiment of connecting plate 106, spanning portion 124 is offset from a plane defined by end 122 of the connecting plate. In one embodiment, spanning portion 124 is offset by at least about 3 mm from a plane defined by end 122 of the connecting plate. In another embodiment, spanning portion 124 is offset by between about 5 mm to about 10 mm from a plane defined by end 122 of the connecting plate.

Figure 5A:
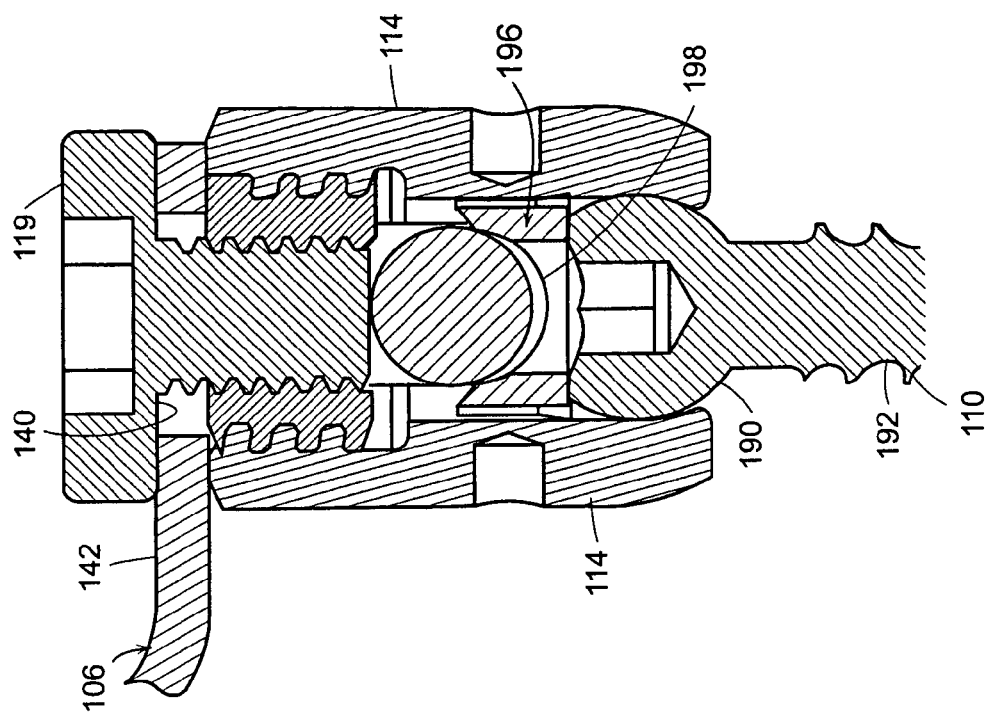
FIG. 5A and FIG. 5B show cross-sections of two embodiments of the system of the present invention that include a polyaxial screw.
Figure 5B:
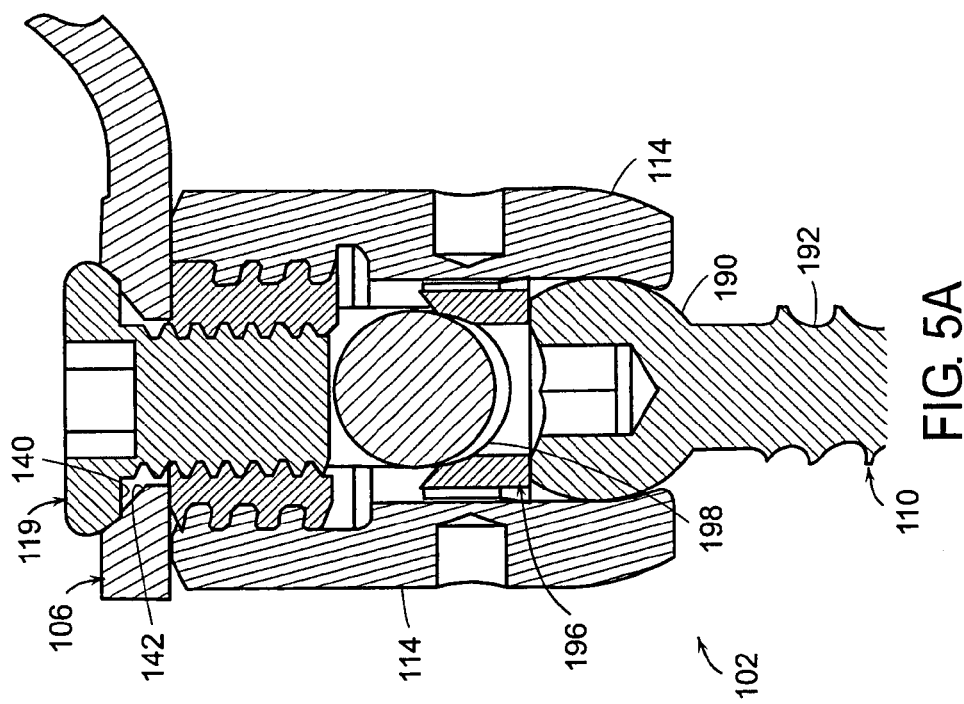

Referring now to FIGS. 5A, B and C, in one embodiment, the present invention is a bone anchor for use with an orthopedic device. The bone anchor of the invention includes distal portion 110 and rod-receiving portion 114, that defines proximal bearing surface 108. In one embodiment of the invention, proximal bearing surface 108 can be selected from the group consisting of an at least partially spherically convex surface, conically convex surface, spherically concave surface and conically concave surface. Preferably, proximal bearing surface 108 is convex. In one embodiment, proximal bearing surface 108 has a radius of curvature between about 5 mm and about 15 mm.

In one embodiment, the bone anchor of the invention is a polyaxial screw. In this embodiment, distal portion 110 includes a bone screw portion 192 and a head 190, connected to the bone screw portion. Head 190 mates with rod receiving portion 114, whereby bone screw portion 192 pivots about a pivot point at head 190 of the bone screw portion 192. The bone anchor can further include compression member 196 that defines rod seat 198, disposed within the rod-receiving portion adjacent to the head of the bone screw portion. During an operation of spinal fixation system 100 that employs this embodiment of a bone anchor, compression member 196 is disposed between rod 104 and head 190 of distal bone anchor portion 110 so that rod seat 198 substantially mates with rod 104.

Figure 5C:
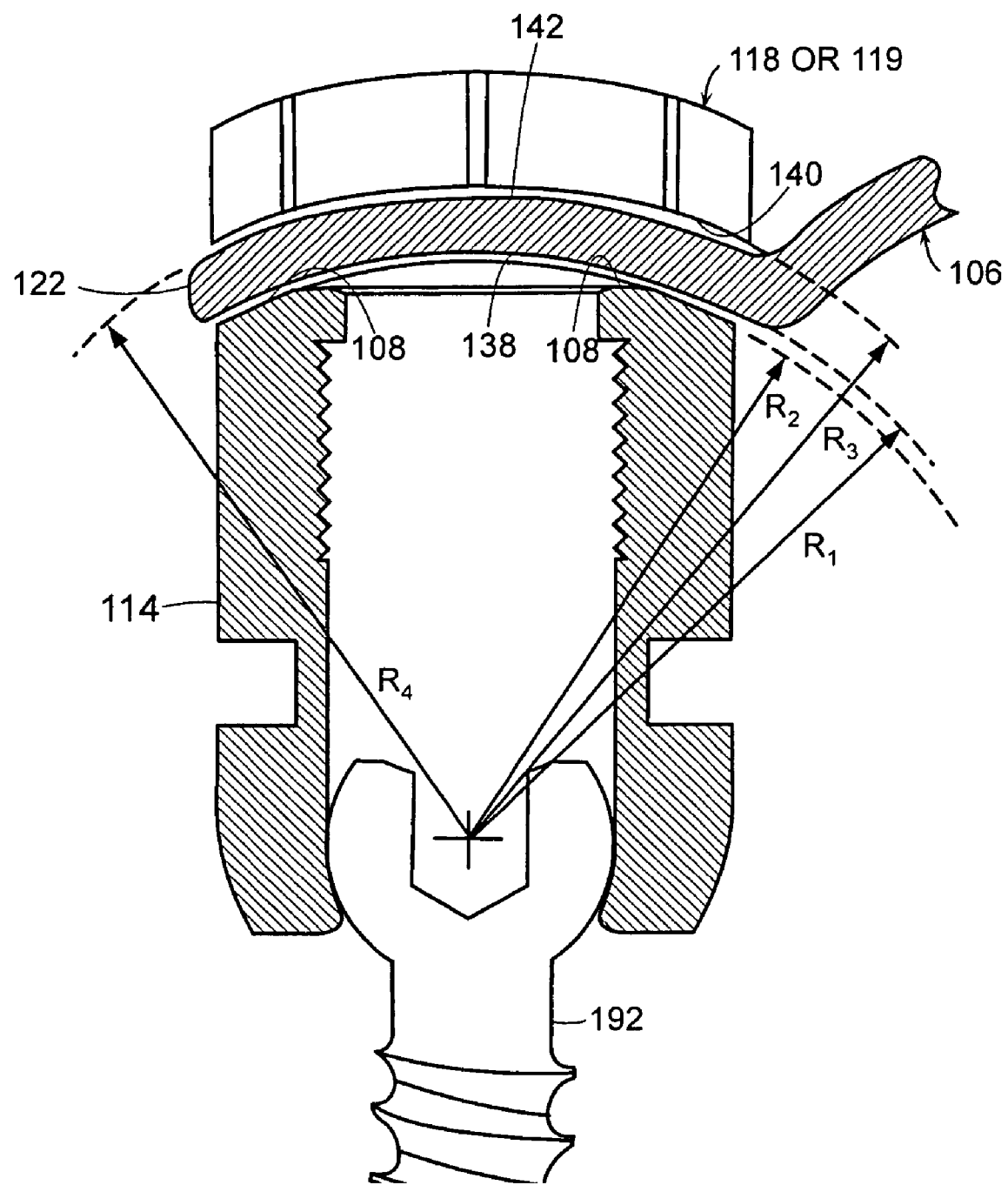
FIG. 5C is a cross-section of a partially assembled system of the present invention that includes a domed bearing surfaces.

Referring now to FIG. 5C, proximal surface 108 of rod receiving portion 114 is spherical and has a radius of curvature R1 that extends from the point about which bone screw portion 192 pivots. Bearing surface 140 of caps 118 or 119 has a radius of curvature R4 that extends from the point about which the bone screw portion 192 pivots. In one embodiment, distal and proximal bearing surfaces 138 and 142, respectively, of connecting plate 106 each have radii of curvature R2 and R3, respectively. In one embodiment, each radius extends from the point about which bone screw portion 192 pivots. In other embodiments, the radii may extend from a point distinct from the pivot point of the bone screw. Each of the radii R1, R2, R3 and R4 can be in a range between about 5 mm and about 15 mm. In alternative embodiments of spanning plates 106, 160, 170 and 180, each of the distal and proximal bearing surfaces, exemplified by surfaces 138 and 142, respectively, in FIGS. 2A-C, can be concave or convex or flat. The bearing surfaces can have various shapes, such as conical or spherical.

Figure 5D:
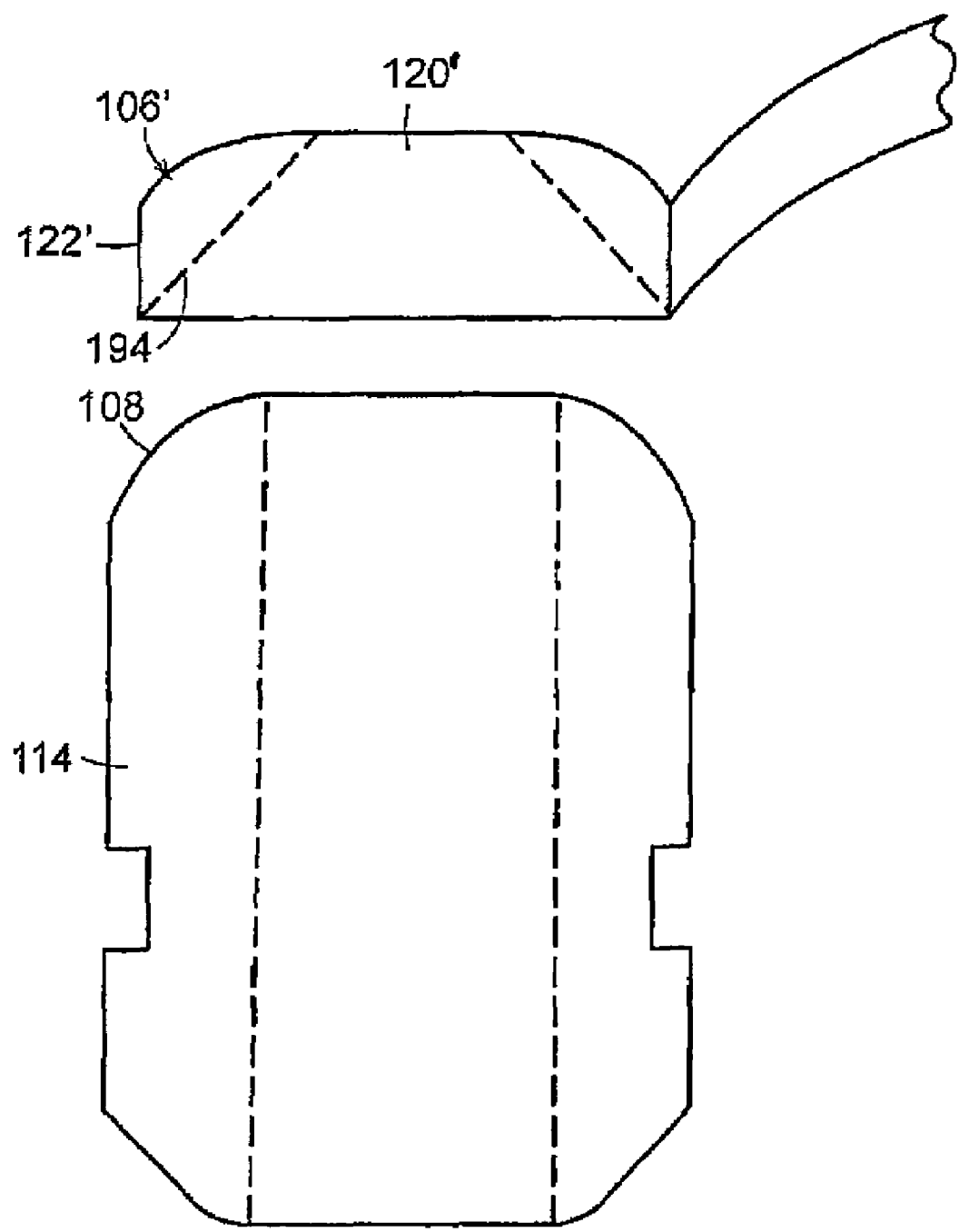
FIG. 5D is a cross-section of an alternative embodiment of a partially assembled system of the present invention that includes a domed bearing surfaces.

In one embodiment, shown in FIG. 5D, connecting plate 106' defines opening 120' at end 122' of the plate wherein the opening has bearing surface 194 that mates with proximal surface 108 of bone anchor 102.

Now referring to FIG. 1A and FIG. 1B, in a preferred embodiment, a fully assembled spinal fixation system of the invention comprises: a first set of at least two bone anchors 102, a second set of at least one bone anchor 102, (c) a fixation element connecting bone anchors 102 of the first set, and connecting plate 106 or an alternative embodiment thereof as described herein, connecting bone anchor 102 of the first set with bone anchor 102 of the second set. In one embodiment, a connecting element is rod 104. At least one anchor 102 includes (i) rod receiving portion 114 that includes proximal bearing surface 108 and (ii) distal portion 110, including bone screw portion 192 and head 190 that mates with rod receiving portion 114. Bone screw portion 192 pivots about a point at head 190.

The fully assembled spinal fixation system further includes a closure mechanism engageable with anchor 102 to fix rod 104 within rod receiving portion 114 of anchor 102. In one embodiment, the closure mechanism includes a set screw 116 or any of its alternative embodiments described herein, which is threadably engageable with rod receiving portion 114, whereby set screw 116 contacts and fixes rod 104 within rod receiving portion 114.

The fully assembled spinal fixation system further includes a cap engageable with the closure mechanism to fix connecting plate 106 to bone anchor 102. In one embodiment, the cap is cap 118 or any of its alternative embodiments described herein. Cap 118, which defines distal bearing surface 140, is threadably engageable with set screw 116, whereby connecting plate 106 is fixed at proximal bearing surface 108 of rod receiving portion 114.

The operation of the present invention will now be described with reference to FIGS. 1A, 1B, 5A and 5B. It will be understood that any alternative embodiments of bone anchors, connecting plates, set screws or caps can be used interchangeably.

During operation of the spinal fixation system of the present invention, a first and a second bone anchors 102 are implanted in a first vertebra and a second vertebra, respectively. The first and second bone anchors 102 are connected with a fixation element, which, in one embodiment, is rod 104. Next, one end 122 of a connecting plate 106 is coupled to a proximal bearing surface 108 of at least a portion of the first bone anchor 102. In one embodiment, the above-described steps are followed by implanting a third bone anchor 102 in the first vertebra on a side of the spine opposite the first bone anchor 102, and coupling connecting plate 106 to proximal bearing surface 108 of the third bone anchor 102.

In another embodiment, a fourth bone anchor 102 is implanted in the second vertebra on a side of the spine opposite the second bone anchor 102, and connecting plate 106 is coupled a to proximal bearing surface 108 of the second bone anchor 102 and to proximal bearing surface 108 of the fourth bone anchor 102.

In one embodiment, bone anchors 102 are implanted in two adjacent vertebrae. Rod receiving portions 114 of each bone anchor 102 are aligned for receiving rod 104. Rod 104 is placed in rod receiving portions 114, thereby connecting bone anchors 102. Set screws 116 are threadably engaged in rod receiving portions 114 of at least a portion of bone anchors 102, thereby fixing rod 104 to bone anchors 102. One end 122 of at least one connecting plate 106 is mated to proximal bearing surface 108 of at least a portion of bone anchors 102. Next, caps 118 are engaged with at least a portion of set screws 116, thereby fixing connecting plate 106 to bone anchors 102. Following the steps described above, a second bone anchor 102 is implanted in a least one vertebra. Connecting plate 106 is fixed to proximal bearing surface 108 of the second bone anchor 102.

In one embodiment of the invention, during the operation of the spinal fixation system described herein, at least two second bone anchors 102 are implanted into at least two vertebra. Next, rod 104 is placed into rod receiving portions 114 of the second bone anchors 102, followed by threadably engaging set screws 116 into rod receiving portion 114 of at least a portion of bone anchors 102, thereby fixing rod 104 to bone anchors 102. In some embodiments, a plurality of connecting plates 106 is fixed to proximal bearing surfaces 108 of at least a portion of the second bone anchors 102. Connecting plates 106 are fixed to proximal bearing surfaces 108 by threadably engaging caps 118 with set screws 116.

Figure 14A:
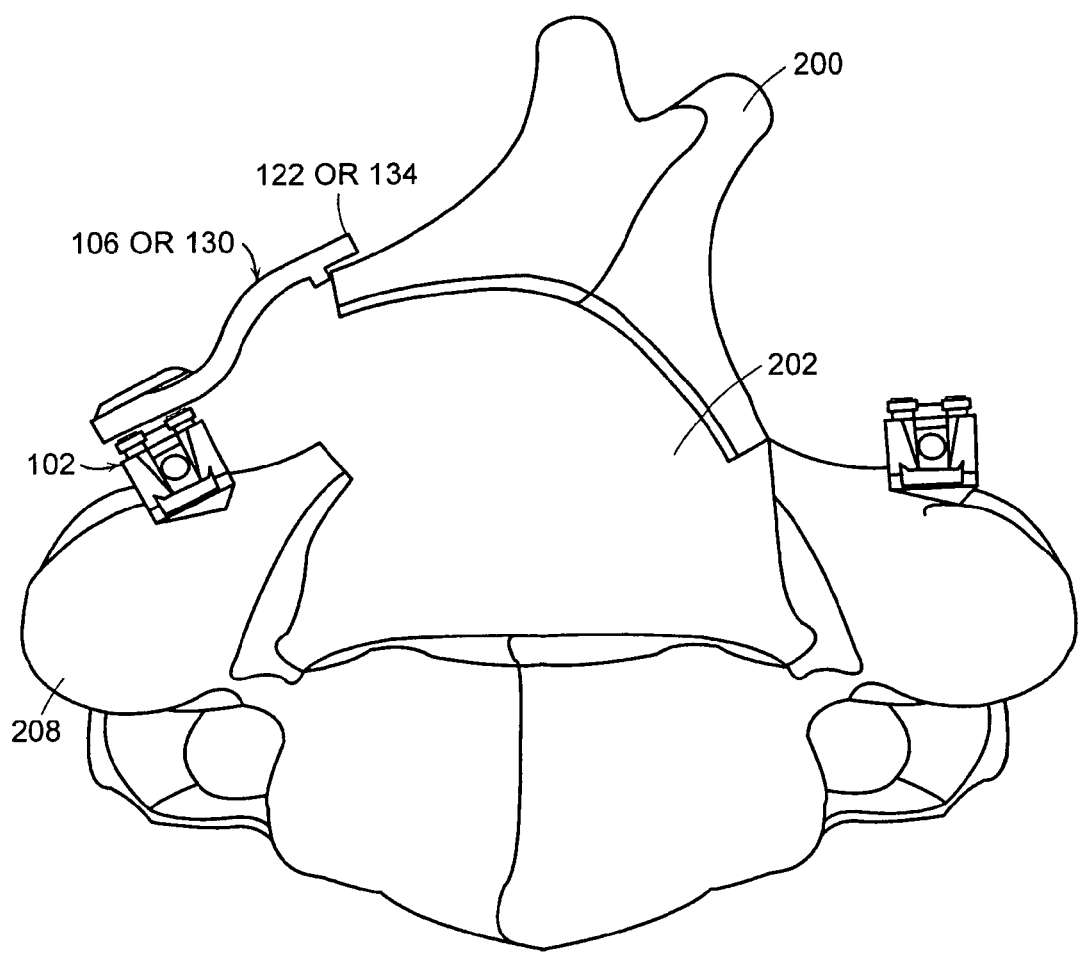
FIG. 14A illustrates the use of a spinal fixation system of the invention to support the spinous process in the rotated position during partial laminoplasty.
Figure 14B:
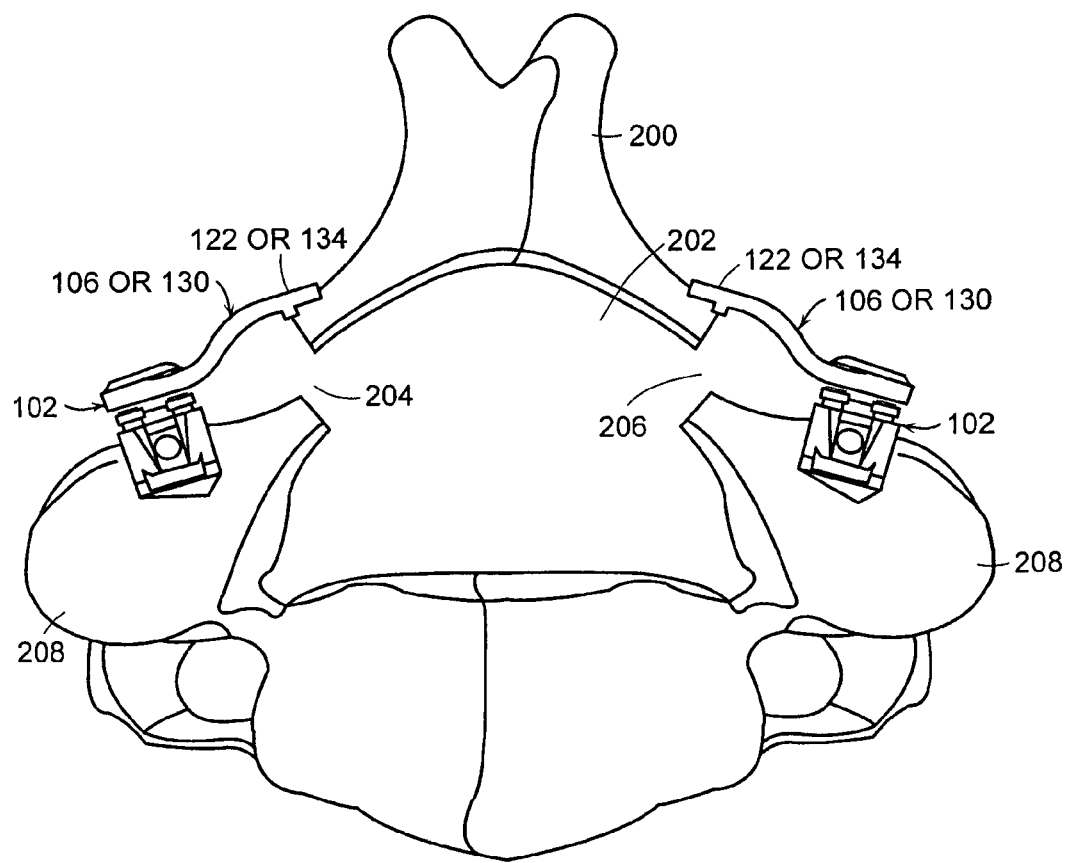
FIG. 14B illustrates the use of a spinal fixation system of the invention to support the spinous process during total laminoplasty.

Now referring to FIGS. 14A and B, in one embodiment, the present invention is a method of decompression of the spinal canal. The method comprises the steps of making a first dissection 204 in posterior element 200 of a vertebra; positioning posterior element 200 of the vertebra to expand spinal canal 202; and maintaining the position of posterior element 200 with a connecting plate (106 or 130) coupled to bone anchor 102 fastened to the vertebra. In one embodiment, posterior element 200 is a portion of the lamina of the vertebra. In another embodiment, posterior element 200 is the spinous process of the vertebra.

The method further includes making a second dissection 206 in posterior element 200, the second dissection being on the contralateral side of the posterior element opposite the first cut. In this embodiment, posterior element 200 with a second connecting plate 106 or 130 coupled to a second bone anchor 102 fastened to the vertebra.

In one embodiment, bone anchors 102 can be fastened to lateral mass 208 of the vertebra. In another embodiment, bone anchors 102 can be fastened to the pedicle of the vertebra.

The method further includes coupling the connecting plate (106 or 130) to posterior element 200.

In one embodiment of this method, embodiment 130 (FIGS. 3A-C) of a connecting plate is used. In this case, posterior element 200 is supported by buttress 132.

In yet another embodiment, the present invention is spinal fixation system 500, as shown in FIG. 15. System 500 comprises bone anchor 502, band clamp 504, bent rod 506 and dovetail threaded post subassembly 508. Other features and methods of operation of system 500 are substantially similar to those disclosed herein for system 100.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A spinal fixation system, comprising:
at least two bone anchors having a bone-engaging portion and a rod receiving portion with opposed arms that receive a rod therebetween;
a rod disposable between the opposed arms of the rod receiving portion of one of the at least two bone anchors; and
a connecting plate having a distal surface that bears against a proximal terminal end surface of each of the opposed arms of the rod receiving portion of at least one of the bone anchors, the connecting plate connecting the at least two bone anchors.

2. The spinal fixation system of claim 1, further including a set screw that extends through the connecting plate and threadably engages the rod receiving portion.

3. The spinal fixation system of claim 2, further including a cap that threadably engages the set screw, whereby the cap fixes the connecting plate to the rod receiving portion of the bone anchor.

4. The spinal fixation system of claim 3, wherein the connecting plate defines an opening at an end and a spanning portion extending from the end, and wherein the set screw or the cap extend through the opening when the connecting plate is fixed to the bone anchor.

5. The spinal fixation system of claim 4, wherein the connecting plate includes a buttress at a distal side of the spanning portion.

6. The spinal fixation system of claim 5, wherein each of two sets of bone anchors are connected by rods and wherein the two sets of bone anchors are connected to each other by connecting plates.

7. The spinal fixation system of claim 4, wherein the proximal surface of the bone anchor has a bearing surface that mates with the connecting plate and wherein the connecting plate has a distal bearing surface that is domed.

8. The spinal fixation system of claim 7, wherein the domed bearing surface of the connecting plate is spherical or conical.

9. The spinal fixation system of claim 8, wherein the cap has a distal bearing surface that is chamfered or domed.

10. The spinal fixation system of claim 9, wherein the connecting plate has a proximal bearing surface that mates with the distal bearing surface of the cap.

11. The spinal fixation system of claim 9, further including a floating washer, the floating washer including a bearing surface that mates with the distal bearing surface of the cap, and rails that slidably engage the connecting plate, whereby the connecting plate is fixed to the bone anchor by compression between the floating washer and the bone anchor.

12. The spinal fixation system of claim 11, wherein the distal bearing surface of the cap is domed.

13. The spinal fixation system of claim 3, wherein the cap threadably engages the set screw at a threaded bore defined by the cap.

14. The spinal fixation system of claim 3, wherein the cap threadably engages a threaded bore defined by the set screw.

15. The spinal fixation system of claim 1, wherein the connecting plate is oriented at an angle in a range between about 20° and about 160° relative to the rod.

16. The spinal fixation system of claim 1, wherein the connecting plate is oriented at an angle in a range between about 60° and about 120° relative to the rod.

17. The spinal fixation system of claim 1, wherein the connecting plate defines an opening at an end and a spanning portion extending from the end.

18. The spinal fixation system of claim 17, wherein each end is fixed to a proximal surface of a bone anchor.

19. The spinal fixation system of claim 17, wherein the spanning portion of the connecting plate is arcuate.

20. The spinal fixation system of claim 19, wherein the spanning portion has a radius of curvature in a range of between about 8 mm and about 12 mm.

21. The spinal fixation system of claim 19, wherein the spanning portion has a radius of curvature in a range of between about 5 mm and 15 mm.

22. The spinal fixation system of claim 17, wherein the spanning portion is offset from a plane defined by the end of the connecting plate.

23. The spinal fixation system of claim 22, wherein the spanning portion is offset at least about 3 mm from the plane defined by the end of the connecting plate.

24. The spinal fixation system of claim 22, wherein the spanning portion is offset between about 5 mm to about 10 mm from the plane defined by the end of the connecting plate.

25. The spinal fixation system of claim 17, wherein the openings defined by the connecting plate each independently have at least a portion of a shape selected from the group consisting of a circle and an ellipse.

26. The spinal fixation system of claim 17, wherein the opening defined by the connecting plate is open-ended.

27. The spinal fixation system of claim 1, wherein the bone anchors are each independently selected from the group consisting of a polyaxial screw, a monoaxial screw and a bolt.

28. The spinal fixation system of claim 27, wherein the bone anchors include at least one polyaxial screw.

29. The spinal fixation system of claim 1, wherein the distal bone anchor portion is a polyaxial screw that includes a head that mates with the rod receiving portion and a bone screw portion, whereby the bone screw portion pivots about a point at the head of the bone screw portion.

30. The spinal fixation system of claim 29, wherein the proximal surface of the rod receiving portion is spherical and has a radius of curvature that extends from the point about which the bone screw portion pivots.

31. The spinal fixation system of claim 30, wherein the connecting plate defines an opening at an end of the plate and wherein the opening has a bearing surface that mates with the proximal surface of the bone anchor.

32. The spinal fixation system of claim 30, further includes a set screw that threadably engages the rod receiving portion and a cap that threadably engages the set screw, the cap including a distal bearing surface that has a radius of curvature that extends from the point about which the bone screw portion pivots.

33. The spinal fixation system of claim 32, wherein the polyaxial screw further includes a compression member between the rod and the head of the distal bone screw portion of the polyaxial screw, the compression member including a rod seat that substantially mates with the rod.

34. A spinal fixation system, comprising:
a first set of at least two bone anchors having a bone-engaging portion and a receiving portion with opposed arms that receive a fixation element therebetween;
a second set of at least one bone anchor;
a fixation element disposable between the opposed arms of the receiving portion of the at least two bone anchors of the first set for connecting the bone anchors of the first set;
a connecting plate connecting a bone anchor of the first set with a bone anchor of the second set, the connecting plate having a distal surface that bears against a proximal terminal end surface of each of the opposed arms of the receiving portion of the bone anchor of the first set; and
a closure mechanism extending through the connecting plate and engaging one of the bone anchors to fix the fixation element within the bone anchor.

35. The spinal fixation system of claim 34, wherein the bone-engaging portion of at least one bone anchor includes a bone screw portion and a head that mates with the receiving portion, whereby the bone screw portion pivots about a point at the head of the bone screw portion.

36. The spinal fixation system of claim 35, further comprising a cap engageable with the closure mechanism to fix the connecting plate to the bone anchor.

37. A method of fixing vertebrae relative to each other, comprising the steps of:
implanting a first bone anchor and a second bone anchor on opposite sides of a first vertebra, each of the first and second bone anchors including opposed arms of a rod receiving portion and each of the opposed arms having a proximal terminal end surface;
disposing a fixation element between the opposed arms of the rod receiving portion of the first bone anchor;
positioning a distal surface of a connecting plate on the proximal terminal end surfaces of each of the opposed arms of the rod receiving portions of the first and second bone anchors; and
inserting a closure mechanism through the connecting plate to engage the rod receiving portion of the first bone anchor.

38. The method of claim 37, further including the steps of:
implanting a third bone anchor in a second vertebra, the third bone anchor including a receiving portion, and
connecting the first and third bone anchors with the fixation element by disposing the fixation element between the opposed arms of the rod receiving portion of the third bone anchor.

39. The method of claim 38, wherein the fixation element is a rod.

40. The method of claim 38, further including the steps of:
implanting a fourth bone anchor in the second vertebra on a side of the spine opposite the third bone anchor, the fourth bone anchor including a proximal bearing surface and coupling a connecting plate to a proximal bearing surface of the third bone anchor and to the proximal bearing surface of the fourth bone anchor.

* * * * *

UNITED STATES PATENT AND TRADEMARK OFFICE
CERTIFICATE OF CORRECTION

PATENT NO. : 7,645,294 B2  Page 1 of 1
APPLICATION NO. : 10/813904
DATED : January 12, 2010
INVENTOR(S) : Kalfas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 760 days.

Signed and Sealed this

Twenty-first Day of December, 2010

David J. Kappos
*Director of the United States Patent and Trademark Office*